(12) United States Patent
Friedman et al.

(10) Patent No.: US 9,072,890 B2
(45) Date of Patent: Jul. 7, 2015

(54) PACING, SENSING OR DEFIBRILLATOR LEADS FOR IMPLANTATION INTO THE MYOCARDIUM

(75) Inventors: Paul A. Friedman, Rochester, MN (US); Charles J. Bruce, Rochester, MN (US); Samuel J. Asirvatham, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 13/393,521

(22) PCT Filed: Sep. 2, 2010

(86) PCT No.: PCT/US2010/047738
§ 371 (c)(1),
(2), (4) Date: Jun. 13, 2012

(87) PCT Pub. No.: WO2011/028949
PCT Pub. Date: Mar. 10, 2011

(65) Prior Publication Data
US 2012/0245665 A1    Sep. 27, 2012

Related U.S. Application Data

(60) Provisional application No. 61/239,640, filed on Sep. 3, 2009.

(51) Int. Cl.
*A61N 1/05*    (2006.01)

(52) U.S. Cl.
CPC ............ *A61N 1/0565* (2013.01); *A61N 1/0573* (2013.01)

(58) Field of Classification Search
CPC ... A61N 1/0573; A61N 1/056; A61N 1/0587; A61N 5/04; A61N 5/045

USPC .................................................. 607/115–128
See application file for complete search history.

(56) References Cited

U.S. PATENT DOCUMENTS

| 4,010,758 A | 3/1977 | Rockland et al. |
| 4,355,642 A | 10/1982 | Alferness |

(Continued)

FOREIGN PATENT DOCUMENTS

| WO | WO-03092799 A1 | 11/2003 |
| WO | WO-2005000398 A2 | 1/2005 |

(Continued)

OTHER PUBLICATIONS

International Search Report for International Application No. PCT/US2010/047738, mailed Feb. 16, 2011.

(Continued)

*Primary Examiner* — Rex R Holmes
(74) *Attorney, Agent, or Firm* — Marshall, Gerstein & Borun LLP

(57) ABSTRACT

An electrical lead for a cardiac device includes a body having a distal end sized for insertion through a catheter, first and second electrodes extending through the body, with each electrode terminating in a tip having proximal and distal ends and arranged to extend to an area of cardiac tissue. The tips include a fully insulated portion on the proximal and distal ends measuring in a range between 5 percent and 40 percent of the lengths of the tips, and further include an uninsulated intermediate section. The tip of the second electrode includes a helical section surrounding the first electrode and has an insulated portion on an inwardly facing portion surface facing toward the first electrode. The tip of the second electrode also includes a fully insulated portion on the proximal and distal ends measuring in the same or similar percentage range.

14 Claims, 26 Drawing Sheets

(56) References Cited

U.S. PATENT DOCUMENTS

| | | | |
|---|---|---|---|
| 4,577,643 A | 3/1986 | Beranek | |
| 4,662,382 A | 5/1987 | Sluetz et al. | |
| 5,020,545 A | 6/1991 | Soukup | |
| 5,022,396 A | 6/1991 | Watanabe | |
| 5,076,285 A | 12/1991 | Hess et al. | |
| 5,246,014 A | 9/1993 | Williams et al. | |
| 5,487,758 A | 1/1996 | Hoegnelid et al. | |
| 5,507,743 A | 4/1996 | Edwards et al. | |
| 5,545,201 A | 8/1996 | Helland et al. | |
| 5,728,140 A | 3/1998 | Salo et al. | |
| 5,755,764 A | 5/1998 | Schroeppel | |
| 5,833,715 A | 11/1998 | Vachon et al. | |
| 5,837,006 A | 11/1998 | Ocel et al. | |
| 6,016,809 A | 1/2000 | Mulier et al. | |
| 6,272,379 B1 | 8/2001 | Fischell et al. | |
| 6,468,263 B1 | 10/2002 | Fischell et al. | |
| 6,497,704 B2 | 12/2002 | Ein-Gal | |
| 6,501,994 B1 * | 12/2002 | Janke et al. | 607/127 |
| 6,716,196 B2 | 4/2004 | Lesh et al. | |
| 6,819,959 B1 | 11/2004 | Doan et al. | |
| 6,923,807 B2 | 8/2005 | Ryan et al. | |
| 6,931,286 B2 | 8/2005 | Sigg et al. | |
| 6,937,897 B2 | 8/2005 | Min et al. | |
| 7,027,876 B2 | 4/2006 | Casavant et al. | |
| 7,103,418 B2 | 9/2006 | Laske et al. | |
| 7,107,096 B2 | 9/2006 | Fischell et al. | |
| 7,120,504 B2 | 10/2006 | Osypka | |
| 7,162,310 B2 | 1/2007 | Doan | |
| 7,177,704 B2 | 2/2007 | Laske et al. | |
| 7,212,870 B1 | 5/2007 | Helland | |
| 7,369,901 B1 | 5/2008 | Morgan et al. | |
| 7,988,690 B2 * | 8/2011 | Chanduszko et al. | 606/49 |
| 2004/0064158 A1 | 4/2004 | Klein et al. | |
| 2004/0068299 A1 | 4/2004 | Laske et al. | |
| 2004/0068312 A1 | 4/2004 | Sigg et al. | |
| 2006/0085042 A1 | 4/2006 | Hastings et al. | |
| 2006/0224224 A1 | 10/2006 | Muhlenberg et al. | |
| 2007/0021745 A1 * | 1/2007 | McIntyre et al. | 606/41 |
| 2008/0294229 A1 | 11/2008 | Friedman et al. | |

FOREIGN PATENT DOCUMENTS

| | | |
|---|---|---|
| WO | WO-2006068880 A1 | 6/2006 |
| WO | WO-2008058265 A2 | 5/2008 |

OTHER PUBLICATIONS

International Preliminary Report on Patentability for International application No. PCT/US2010/047738, dated Mar. 6, 2012.

Written Opinion for International application No. PCT/US2010/047738, dated Mar. 6, 2012.

Cesario et al., "Azygos vein lead implantation: a novel adjunctive technique for implantable cardioverter defibrillator placement," *J. Cardiovasc. Electrophysiol.*, 2004, 15:780-783.

Mohri et al., "Cardiac contractility modulation by electric currents applied during the refractory period," *Am. J. Physiol. Heart Circ. Physiol.*, 2002, 282:H1642-1647.

Sabbah et al., "Cardia contractility modulation with the impulse dynamics signal: studies in dogs with chronic heart failure," *Heart Fail. Rev.*, 2001, 6:45-54.

* cited by examiner

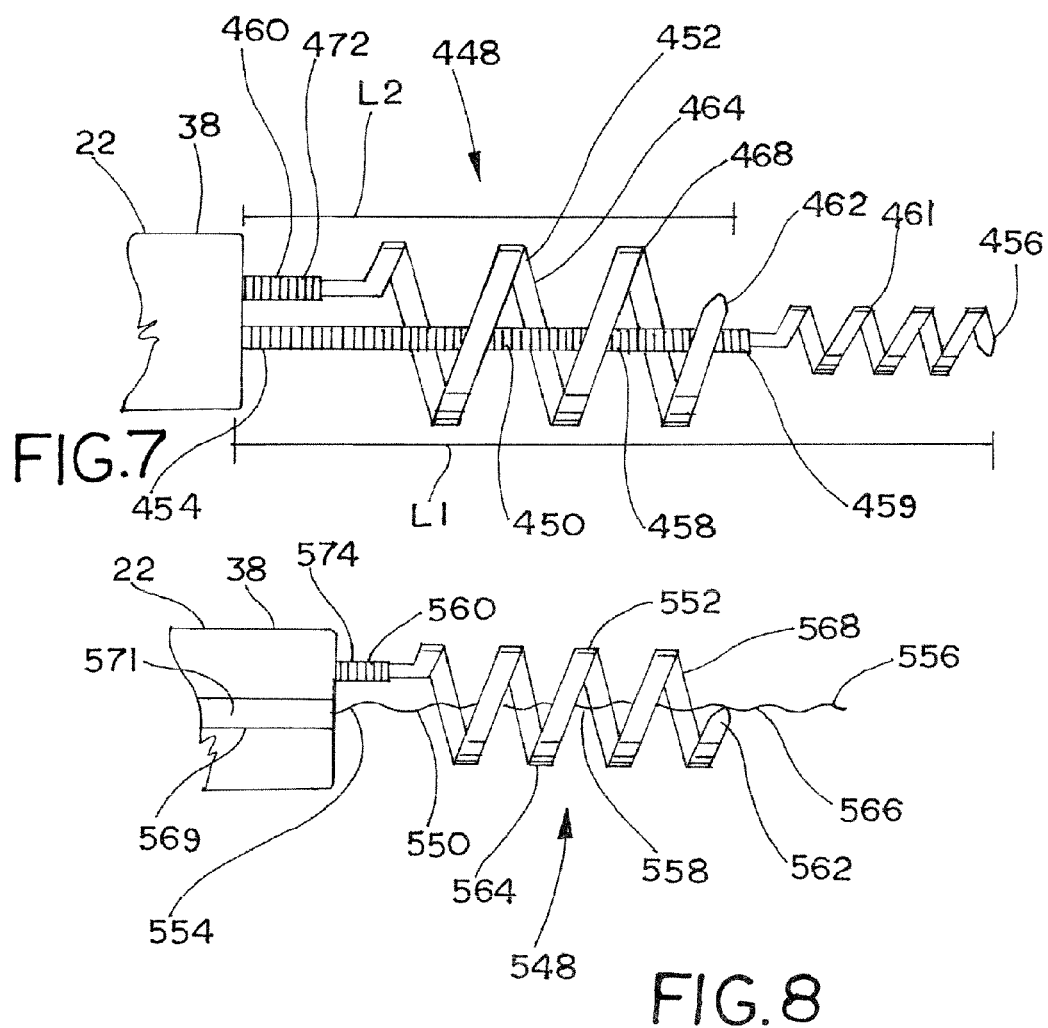

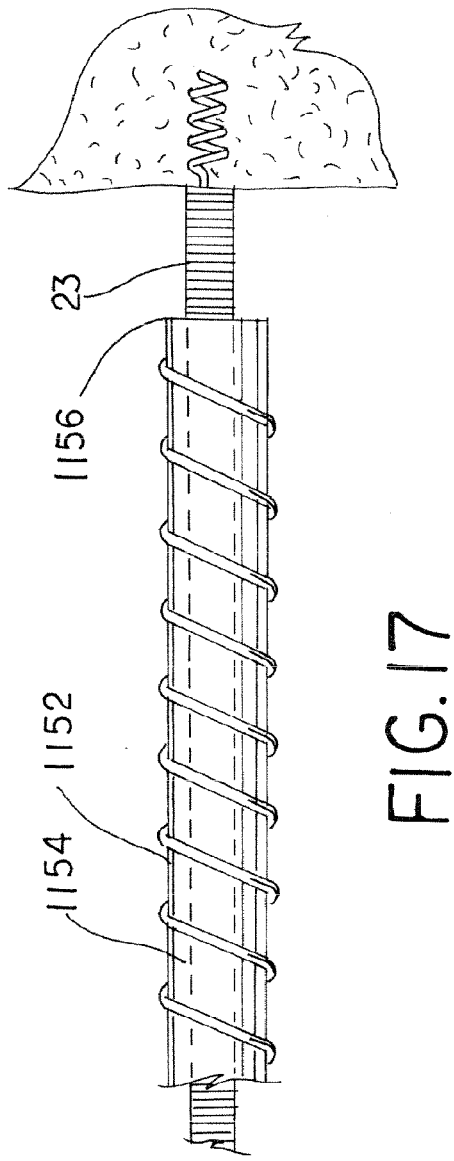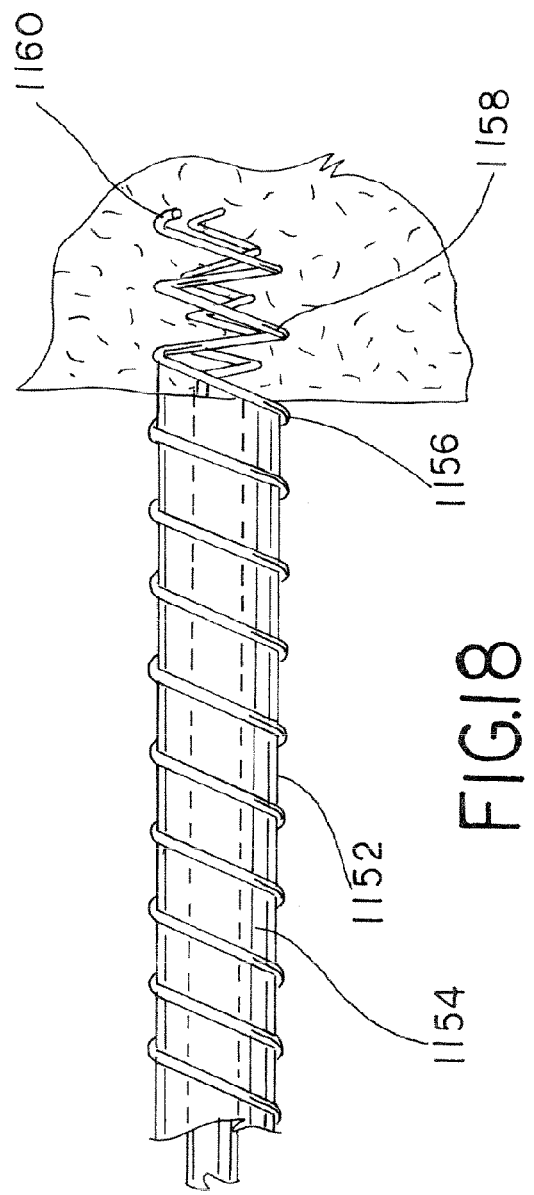

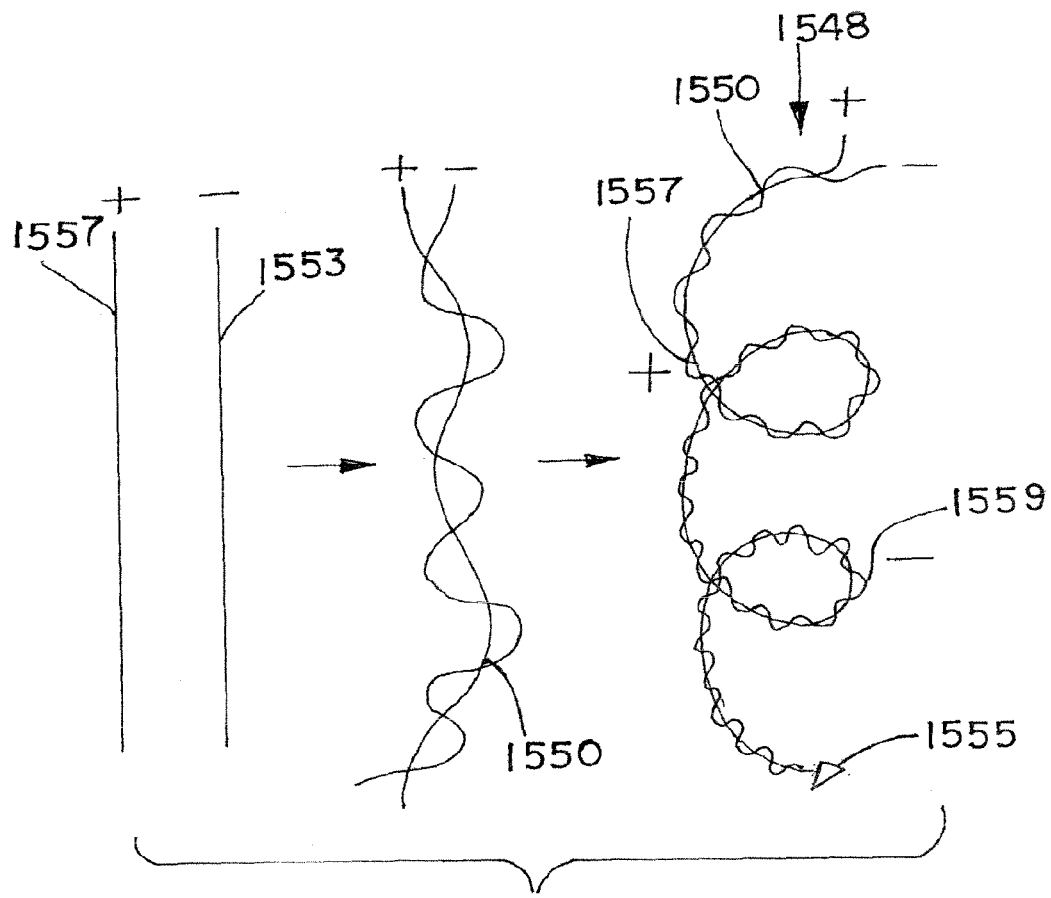
FIG. 26
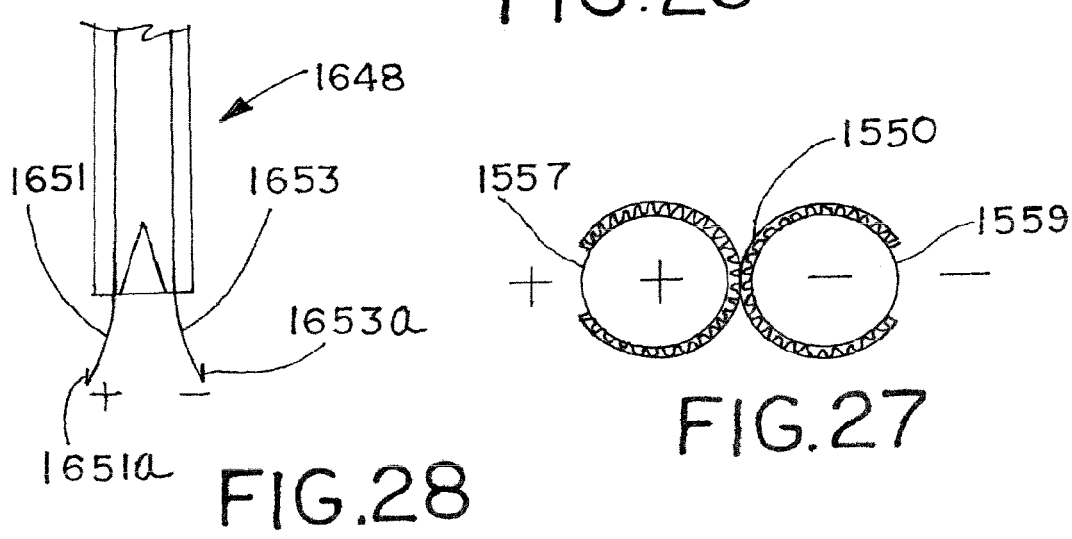
FIG. 28
FIG. 27

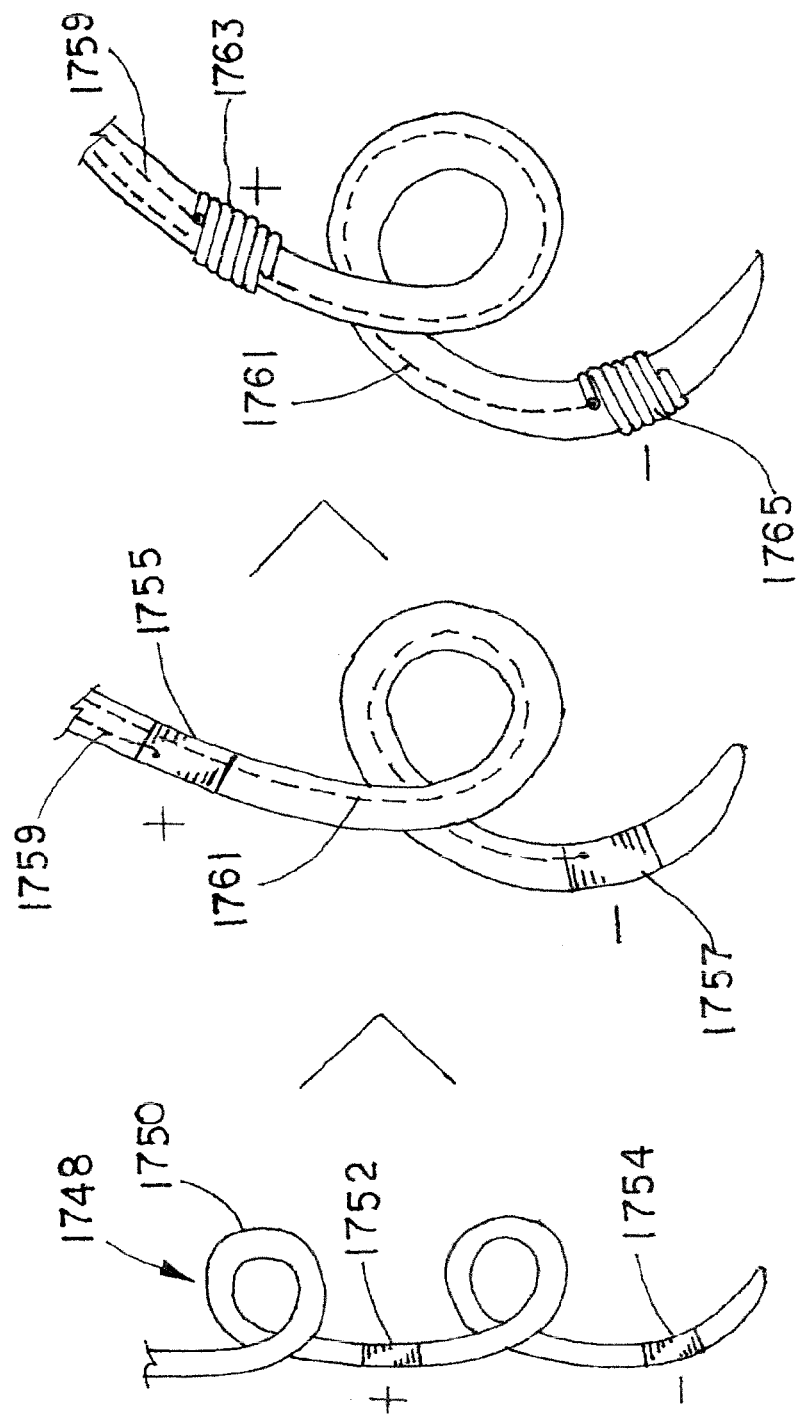

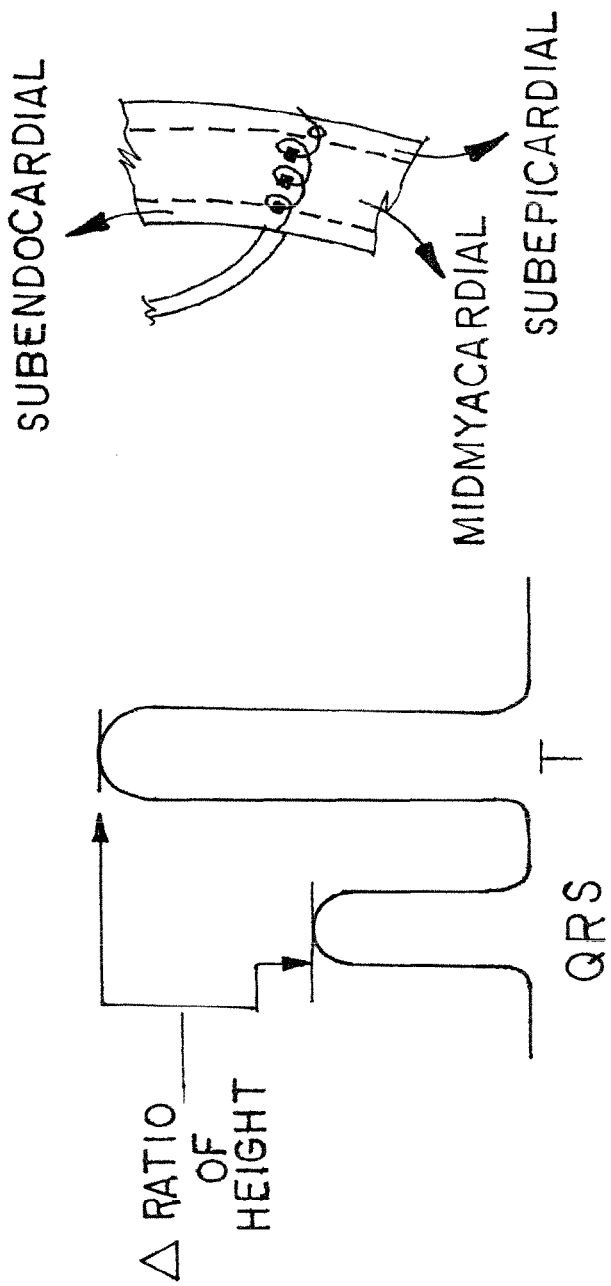

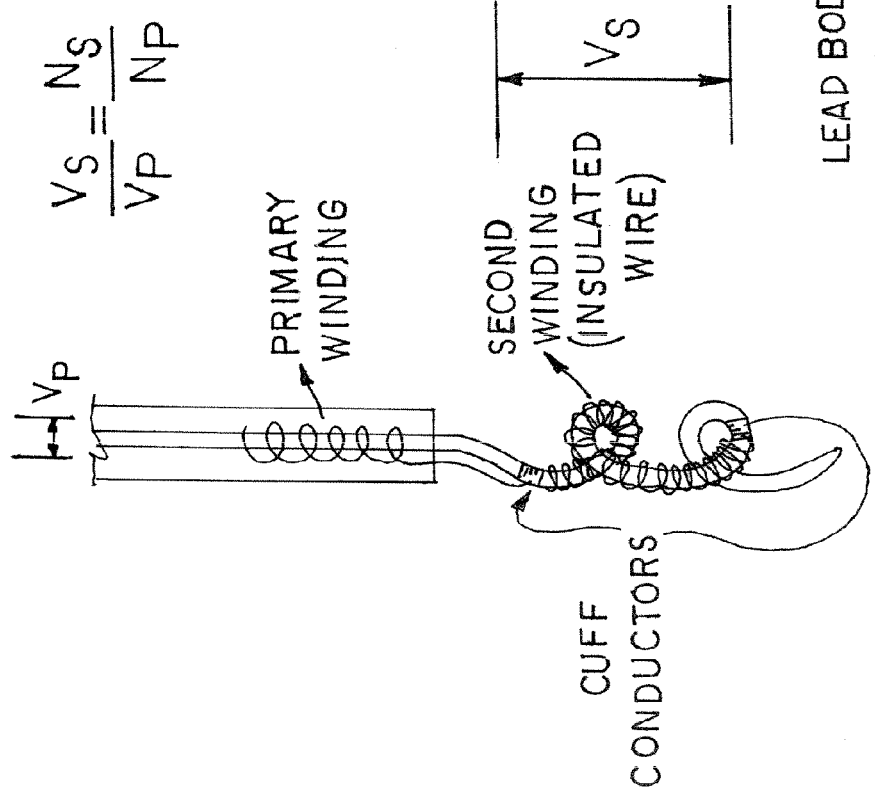
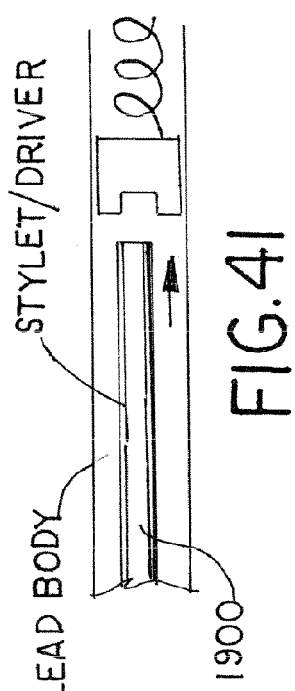
FIG. 40
FIG. 41

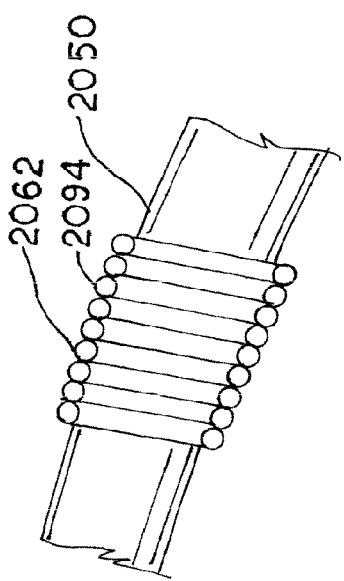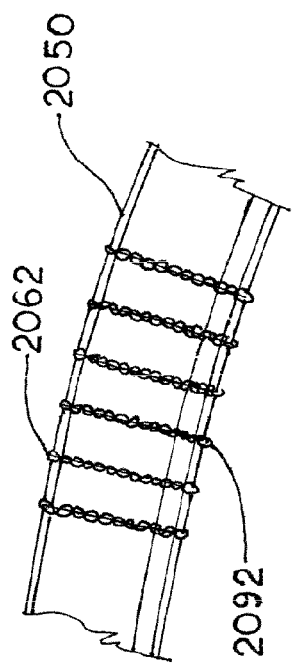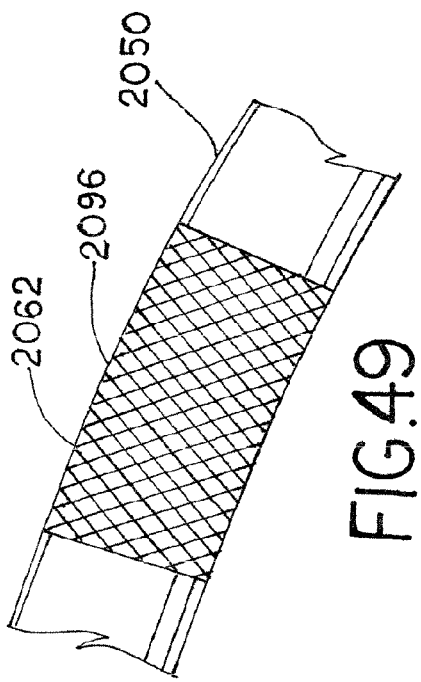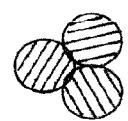

PACING, SENSING OR DEFIBRILLATOR LEADS FOR IMPLANTATION INTO THE MYOCARDIUM

RELATED APPLICATIONS

This application is a U.S. National Phase of PCT/US2010/047738, filed Sep. 2, 2010, which claims priority benefit under 35 U.S.C. §119(e) to U.S. Provisional Patent Application No. 61/239,640, filed Sep. 3, 2009. The entirety of both PCT/US2010/04773 and U.S. Patent Application No. 61/239,640 are hereby incorporated by reference herein.

FIELD OF THE INVENTION

The present invention relates generally to implantable leads for cardiac devices having pacing, sensing, and/or defibrillator leads and, more specifically, to improved tips for such leads.

BACKGROUND OF THE INVENTION

In the field of implantable cardiac devices implantable cardiac devices, implantable systems typically employ various leads for sensing and pacing cardiac activity, and for delivering electrical impulses for defibrillation. As is known, the leads are electrical conductors, typically covered with suitable coatings, and are placed at a desired location within the heart in order to deliver electrical impulses or sense of electrical activity at the appropriate location. The leads may be arranged linearly or coaxially, and are typically delivered using a variety of known delivery sheaths or catheters.

SUMMARY OF THE INVENTION

In accordance with an aspect of the invention, an electrical lead for a cardiac device includes a lead body having a proximal end and a distal end and sized for insertion through a lumen of a steerable catheter. First and second electrodes are provided having opposite polarity and extend through the lead body, with the first and second electrodes each terminating in a tip having a proximal end, a distal end, and an effective length, and with the tip of the first and second electrodes arranged to extend from the lead body for insertion into an area of cardiac tissue. The tip of the first electrode includes a fully insulated portion on the proximal end and a fully insulated portion on the distal end, with each of the fully insulated portions measuring in a range between 5 percent and 40 percent of an effective length of the tip of the first electrode. The tip of the first electrode further includes an intermediate section having an uninsulated portion. The tip of the second electrode includes a helical section surrounding a portion of the tip of the first electrode, the helical section having an outwardly facing portion facing away from the first electrode and an insulated inwardly facing portion facing toward the first electrode. The tip of the second electrode includes a fully insulated portion on the proximal end and a partially insulated portion extending from the fully insulated portion toward the distal end, with the fully insulated portion on the proximal end measuring in a range between 5 percent and 40 percent of an effective length of the tip of the second electrode.

In further accordance with one or more preferred forms of the invention, the tip of the first electrode may be linear, and the helical portion of the second electrode surrounds a portion of the first electrode. The effective length of the tip of the first electrode is less than the effective length of the tip of the second electrode, and may be about 75 percent of the effective length of the tip of the second electrode. The intermediate section of the tip of the first electrode may include insulation, and a partially uninsulated portion of the intermediate section may be formed by a plurality of perforations through the insulation. The helical portion of the tip of the second electrode may form or otherwise serve as an anchor arranged to secure the distal end of the lead body adjacent the area of cardiac tissue. The partially insulated portion of the helix includes no insulation on the outwardly facing surface. Each of the fully insulated portions of the tip of the first electrode measures from 5 percent to no more than 15 percent. Still preferably, one or more of the preferred forms disclosed herein mat permit placement of two electrodes of opposite polarity within the myocardium via a single lead, thus permitting intramyocardial stimulation with the absence of an electrode, such as a ring electrode, within a cardiac chamber.

In accordance with another exemplary form of the invention, an electrical lead for a cardiac device includes a lead body having a proximal end and a distal end, with the lead body sized for insertion through a lumen of a steerable catheter. An anchor is arranged to secure the distal end of the lead body into cardiac tissue, and a first electrode and a second electrode are provided having opposite polarity and extend through the lead body. The first and second electrodes each terminate in a tip having a proximal end, a distal end, and an effective length, with the tip of the first and second electrodes arranged to extend from the lead body for insertion into the area of cardiac tissue. The tip of each of the first and second electrodes includes a fully insulated portion on the proximal end, a fully insulated portion on the distal end, with each of the fully insulated portions on both the proximal and distal ends having an insulated length measuring between 5 percent and 40 percent of an effective length of the tip. The tip of each of the first and second electrodes further includes an intermediate section between the proximal and distal ends having an uninsulated portion.

In accordance with still further exemplary forms of the invention, the tip of the second electrode may include a helical section surrounding a portion of the tip of the first electrode, with the tip of the second electrode including a fully insulated portion on the proximal end and an uninsulated portion extending from the fully insulated portion toward the distal end, and with the fully insulated portion on the proximal end measuring in a range between 5 percent and 40 percent of an effective length of the tip of the second electrode. Alternatively, the tip of the first electrode may include a fully insulated linear proximal end and an uninsulated helical distal end, and the tip of the second electrode may have a helical shape and include a fully insulated portion measuring in a range between 5 percent and 40 percent of an effective length of the tip of the second electrode. A portion of the tip of the second electrode may surround the linear proximal end of the tip of the first electrode. The first tip may be formed of a wire suture housed within a hollow lumen of a retractable central delivery pin, and the first tip may be sized to extend into the area of cardiac tissue upon retraction of the delivery pin. As another alternative, an anchor may secure a tip assembly adjacent to the area of cardiac tissue, and each the first tip and the second tip may include a plurality of outwardly extending bristles disposed adjacent the insulated distal end. The tip alternatively may include a pin arranged to extend from the lead body in a position adjacent the area of cardiac tissue, and may carry a first expandable electrode in electrical communication with the first electrode and a second expandable electrode in electrical communication with the second electrode, with each of the first and second expandable electrodes capable of being delivered through the lead body in a collapsed state and deployable into cardiac tissue, at or adjacent the desired area of cardiac tissue. Such electrodes may be formed of a memory material. Finally, an insulated tip may carry the first and second electrodes and may comprise a wire suture, with the first and second electrodes spaced apart on the tip. The tip and the first and second electrodes are sized to extend through a lead body having a proximal end and a distal end and sized for insertion through a lumen of a steerable catheter to allow placement of the first tip and the second tip adjacent an area of cardiac tissue.

In accordance with a further exemplary aspect, an electrical lead assembly for use with a cardiac device includes an insulated helix structure, the helix structure arranged to be embedded into an area of cardiac tissue, and a first electrode and a second electrode operatively carried by the helix structure, with the first and second electrodes spaced apart from one another along the helix structure and electrically insulated from one another. The helix structure and the first and second electrodes are sized to extend through a lead body having a proximal end and a distal end, with the lead body sized for insertion through a lumen of a steerable catheter to allow placement of the first tip and the second tip adjacent the area of cardiac tissue. The first electrode is operatively coupled to a first wire extending through an interior portion of the helix structure, with the first electrode comprising a first externally mounted conductive portion disposed about a first exterior portion of the helix. The second electrode is operatively coupled to a second wire extending through the interior portion of the helix structure, with the second electrode comprising a second externally mounted conductive portion disposed about a second exterior portion of the helix.

In accordance with a yet further aspect, an electrical lead assembly for use with a cardiac device includes a conductive helix structure, the helix structure arranged to be embedded into an area of cardiac tissue, the helix structure having an insulated portion and an uninsulated portion, a first electrode formed by the uninsulated portion of the helix structure, a second electrode operatively carried by the insulated portion of the helix structure, and with the first and second electrodes spaced apart from one another along the helix structure and electrically insulated from one another. The helix structure and the first and second electrodes are sized to extend through a lead body having a proximal end and a distal end, the lead body sized for insertion through a lumen of a steerable catheter to allow placement of the first tip and the second tip adjacent the area of cardiac tissue. Insulation preferably ensures that the first wire does not contact the helix, and the electrode mounted on the helix is electrically insulated from the helix, although mechanically the electrode may be embedded so as to form a single mechanical helix. The second electrode is operatively coupled to a wire extending through an interior portion of the helix structure, the second electrode comprising an externally mounted conductive portion disposed about a first exterior portion of the helix.

In accordance with an additional aspect, an electrical lead assembly for use with a cardiac device includes a helix, at least a portion of the helix arranged to be embedded into an area of cardiac tissue and with the helix having an insulated portion and a non-insulated tip, the non-insulated tip forming a first electrode. A coil covers at least a portion of the insulated portion of the helix, with the coil including an insulated portion and a non-insulated portion, the non-insulated portion extending distally past the insulated portion of the coil, with the non-insulated portion forming a second electrode. The first electrode and the second electrode spaced apart from one another by an exposed section of the insulated portion of the helix, and the helix and the first and second electrodes are sized to extend through a lead body having a proximal end and a distal end, the lead body sized for insertion through a lumen of a steerable catheter to allow placement of the first and second electrodes into the area of cardiac tissue. The first electrode is operatively coupled to a first wire extending through the lead body and arranged for operative coupling with the cardiac device, and the second electrode is operatively coupled to a second wire extending through the lead body and arranged for operative coupling with the cardiac device.

In accordance with a still further aspect, an electrical lead for a cardiac device includes a lead body having a proximal end and a distal end, the lead body sized for insertion through a lumen of a steerable catheter, a helix operatively coupled to the lead body adjacent the distal end, at least a portion of the helix arranged to anchor the lead body to an area of cardiac tissue, with the helix having a proximal insulated portion and a non-insulated portion adjacent a distal tip, the non-insulated portion forming a first electrode. A coil covers at least a portion of the insulated portion of the helix, with the coil having a proximal insulated portion and a non-insulated exposed portion, the non-insulated exposed portion extending distally past the proximal insulated portion of the coil, the non-insulated exposed portion forming a second electrode. The first electrode and the second electrode are spaced apart from one another by an exposed section of the insulated portion of the helix, and the helix and the first and second electrodes are sized to extend from the distal end of the lead body. The first electrode is operatively coupled to a first wire extending through the lead body and arranged for operative coupling with the cardiac device, and the second electrode is operatively coupled to a second wire extending through the lead body and arranged for operative coupling with the cardiac device. The first and second wires are insulated from one another throughout a length of the lead body.

BRIEF DESCRIPTION OF THE DRAWINGS

FIG. 7 is an enlarged fragmentary view of the distal end of the lead body and showing a lead tip assembled in accordance with the teachings of a fifth disclosed example of the present invention.

FIG. 8 is an enlarged fragmentary view of the distal end of the lead body and showing a lead tip assembled in accordance with the teachings of a sixth disclosed example of the present invention.

FIG. 17 is an enlarged fragmentary view of the enlarged delivery sheath disposed adjacent a distal end of the existing lead body but shown in an unanchored state.

FIG. 18 is an enlarged fragmentary view similar to FIG. 17 but showing the delivery sheath for the ICD coil in an anchored state secured to an area of cardiac tissue, such as the AVS.

FIGS. 26a, 26b and 26c are elevational views of a braided helix lead tip assembled in accordance with the teachings of another disclosed example of the present invention.

FIG. 27 is an enlarged cross-sectional view of the braided helix lead tip of FIGS. 26a-c and illustrating portions of the exterior insulation removed to expose areas of opposite polarity.

FIG. 28 is an enlarged fragmentary view illustrating the distal end of a delivery sheath for delivering a two-wire lead tip and having an internal ramp to direct the distal ends of the wires.

FIG. 29 is an elevational view of a lead tip assembled in accordance with the teachings of yet another disclosed example of the present invention and having a nonconductive helix structure carrying a pair of electrodes in the form of coils attached to, formed on, or otherwise secured or adhered to the nonconductive helix.

FIG. 30 is an enlarged fragmentary view of the nonconductive helix lead tip of FIG. 29 in which insulated wires run through the helix to corresponding externally mounted cuffs.

FIG. 31 is an enlarged fragmentary view of the nonconductive helix lead tip of FIG. 29 in which insulated wires run through the helix to corresponding externally mounted coils formed from of a series of wire loops wound around the nonconductive helix.

FIG. 38 is a graphical depiction of cardiac activity and illustrating the relationship between R wave amplitude and T wave amplitude.

FIG. 39 is an enlarged fragmentary schematic view in section illustrating a lead tip having a plurality of electrodes or electrode pairs disposed at various positions relative to the distal end of the deployment instrument and shown with various electrodes or electrode pairs disposed in different areas of the relevant cardiac tissue, such as the sub-endocardium, the mid-myocardium, and/or the sub-epicardium.

FIG. 40 is an enlarged fragmentary view of an exemplary delivery sheath and corresponding helical lead tip protruding from the delivery sheath, in which the delivery sheath or other delivery instrument includes a primary winding while the helical lead tip includes a secondary winding to enable the voltage at the lead tip to be stepped up according to known electrical principles.

FIG. 41 is an enlarged fragmentary view in section of a retractable drive mechanism for embedding any one of the foregoing helical or helix-shaped lead tips into desired tissue, and having a retractable stylet/driver which is releasably engageable with the lead tip and which is arranged to rotationally drive the lead tip according to a known mechanical ratio, such as a 1:1 drive ratio.

FIG. 47 is an enlarged fragmentary elevational view of a portion of the helix of FIGS. 43 and 44 having an exemplary braided coil arrangement surrounding the portion of the helix.

FIG. 47A is a cross-sectional view of the braided coil of FIG. 47.

FIG. 48 is an enlarged fragmentary elevational view of a portion of the helix of FIGS. 43 and 44 having an exemplary three-wire coil arrangement surrounding the portion of the helix.

FIG. 48A is a cross-sectional view of the three-wire arrangement of FIG. 48.

FIG. 49 is an enlarged fragmentary elevational view of a portion of the helix of FIGS. 43 and 44 having an exemplary wire mesh coil arrangement surrounding the portion of the helix.

DESCRIPTION OF THE PREFERRED EMBODIMENTS

Figure 1:
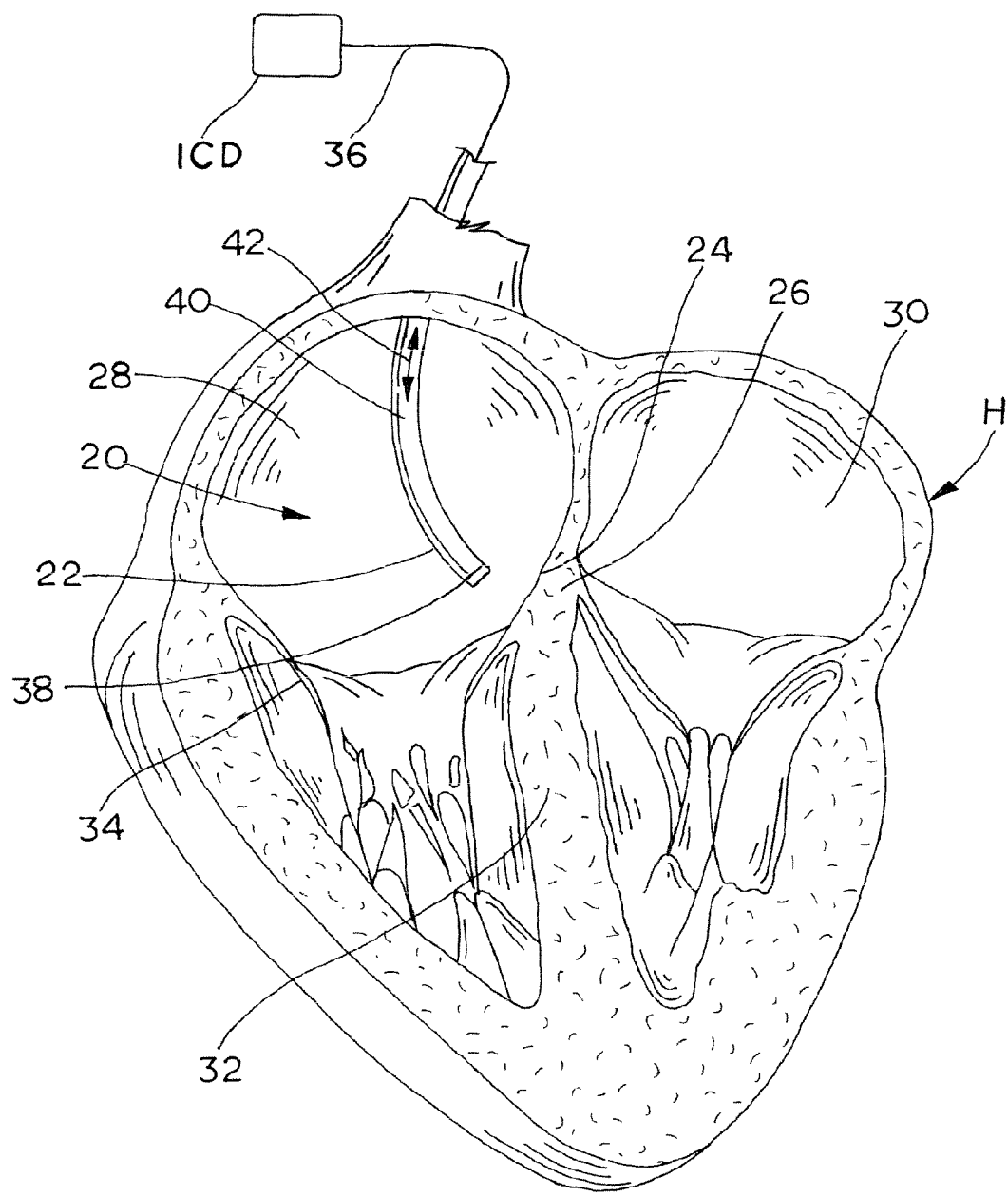
FIG. 1 is a cross-sectional diagram of a heart illustrating the deployment of a bipolar pacing, sensing, or defibrillating lead via a lead body to the atrial ventricular septum.

Referring now to the drawings, FIG. 1 illustrates an exemplary lead deployment system 20 for deploying an electrical lead 21 (obscured in FIG. 1 but shown in FIG. 2) having a lead body 22 to cardiac tissue located at a desired area 24 on the atrioventricular septum (AVS) 26 within a heart H. The heart H includes a right atrium 28, a left atrium 30, an area of the myocardium 32, and a tricuspid valve 34. The lead body 22 includes a proximal end 36 illustrated schematically in FIG. 1, and a distal end 38. The proximal end 36 is shown connected to an implantable cardiac device or ICD. The lead body 22 typically includes a lumen 40, which typically houses at least two conductors (describing greater detail below with respect to, for example, FIG. 2) which run through the lumen 40, generally along an axis 42 of the lumen 40. The lumen 40 is typically part of a steerable catheter of the type commonly employed in the relevant art. A more complete description of the exemplary lead deployment system 20 can be found in co-pending U.S. Provisional Patent Application No. 60/753,098, filed Dec. 25, 2005, and U.S. Non-provisional patent application Ser. No. 12/131,756, filed Jun. 2, 2008, the entire disclosures of which are hereby incorporated by reference herein.

Figure 2:
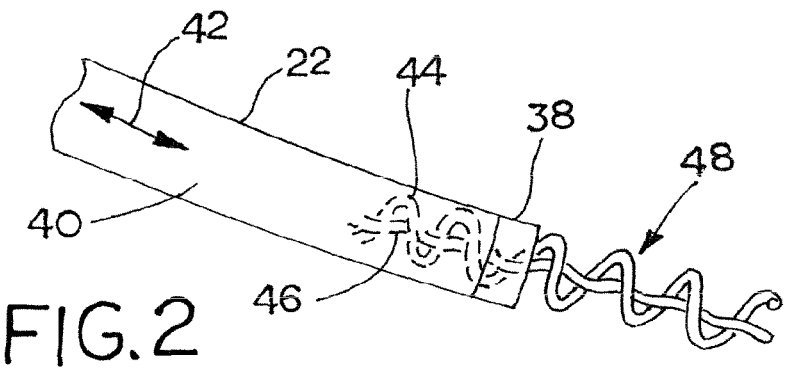
FIG. 2 is an enlarged fragmentary view of a bipolar pacing lead assembled in accordance with the teachings of the present invention and illustrating an exemplary lead body terminating in lead tips for insertion in the myocardium at, for example, the atrial ventricular septum or at other suitable locations, with each of the lead tips electrically coupled to a corresponding electrode.

Referring now to FIG. 2, the distal end 38 of the lead body 22 is shown in greater detail. An electrode 44 and an electrode 46 are shown within the lumen 40 of the lead body 22. The shape, arrangement, and/or the orientation for the electrodes 44 and 46 as shown are exemplary only. Those of skill in the art will understand that the electrodes 44 and 46 may take any suitable form, and that electrodes 44 and 46 connect the ICD to a tip structure 48, with at least portions of the tip structure 48 being structured for insertion or implantation into the desired area 24 of cardiac tissue as will be discussed in greater detail below. Those of skill in the art will also understand that the electrode 44 and 46 will have opposite polarity relative to one another. Those of skill in the relevant art will understand that the implantable leads discussed herein may be used with a variety of cardiac devices and may function as pacing leads, sensing leads, and/or leads for defibrillators.

Figure 3:
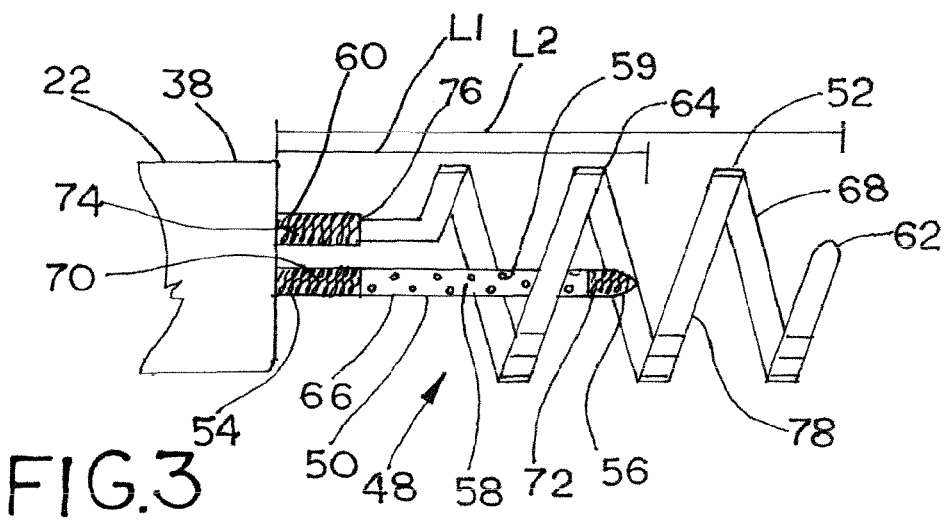
FIG. 3 is an enlarged fragmentary view of the distal end of the lead body showing a lead tip assembled in accordance with the teachings of a first disclosed example of the present invention.

Referring now to FIG. 3, the tip structure 48 is shown in greater detail and is assembled in accordance with the teachings of a first disclosed example of the present invention. The tip structure 48 is shown attached to the distal end 38 of the lead body 22, with a first tip 50 and a second tip 52 protruding from the distal and 38 of the lead body 22. The first tip 50 preferably is electrically coupled to the electrode 44, while the second tip 52 is electrically coupled to the electrode 46. The first tip 50 includes a proximal end 54, a distal end 56 and an intermediate portion 58. The second tip 52 also includes a proximal end 60, a distal end 62, and an intermediate portion 64. In the embodiment of FIG. 3, the first tip 50 is in the form of a linear pin 66, while the second tip 52 is in the form of a helix 68, with the linear pin 66 having an effective length L1 and with the helix 68 having an effective length L2. According to the exemplary form of FIG. 3, the effective length L2 is greater than the effective length L1. In one preferred form, effective length L1 is approximately 75% of the effective length L2. The effective length may be the overall length of the helix, rather than the length measured along the circuitous path of the curving helix. The effective length may be measured in the undeployed state, because it could be hard to measure the effective length when actually implanted. Those of skill in the art will understand that the tips 50 and 52 are intended to extend from the distal end 38 of the lead body 22 such that the tips 50 and 52 are inserted into the area 24 of cardiac tissue.

Referring still to FIG. 3, the tip 50 includes an insulated portion 70 adjacent the proximal end 54 and an insulated portion 72 adjacent the distal end 56. In the example of FIG. 3, the insulated portions 70 and 72 are fully insulated, and the intermediate portion 58 is uninsulated. As an alternative, the intermediate portion 58 may be partially insulated, and the partially insulated portion may include an insulated layer having a plurality of perforations 59 through the insulation. Preferably, the exposed area of a pin or pins may lie in the range of 10% to 90% of the pin area. Preferably, each of the insulated portions 70 and 72 has a length measuring in a range between 5% and 40% of the effective length L1 of the first tip 50. Still preferably, each of the insulated portions 70 and 72 has a length measuring about 15% of the effective length L1, or alternatively from 5% to no more than 15% of the effective length L1. The helix 68 of the second tip 52 winds around the first tip 50 so as to surround a portion of the first tip 50, and the second tip 52 includes an insulated portion 74 adjacent the proximal end 60. In the example of FIG. 3, the insulated portion 74 is fully insulated, and measures in a range between 5% and 40% of the effective length L-2 of the second tip 52. The insulated portion 74 includes an end 76, at which point the insulation transitions to a partially insulated portion 78.

Figure 3A:
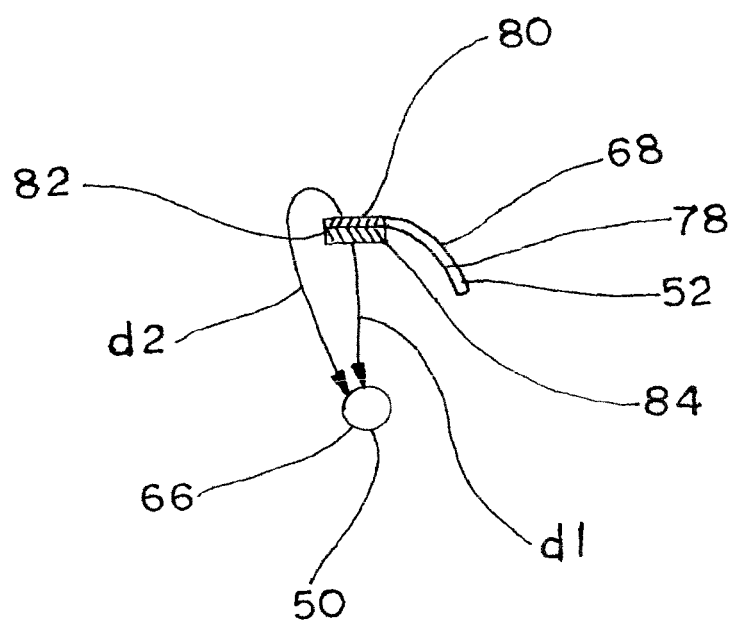
FIG. 3A is a cross-sectional view taken along line 3A-3A of FIG. 3, and illustrates a partially insulated helix having insulation on the portion of the helix that faces the centrally located tip or pin.

Referring now to FIG. 3A, a portion of the helix 68 and a portion of the linear pin 66 are shown. The helix 68 includes an upwardly facing surface 80 facing away from the linear pin 66 of the first tip 50, and further includes an inwardly facing surface 82 facing toward the linear pin 66 of the first tip 50. The partially insulated portion 78 is formed by a layer of insulation 84 formed or otherwise suitably applied to the inwardly facing surface 82 of the helix 68. In accordance with the disclosed example, the current between the first and second tips 50 and 52 must travel the distance d2 due to the insulation, and the distance d2 is greater than the actual distance between the tip pin 66 and the helix 68. Such an arrangement may allow electrical impulses to capture a greater area of tissue.

In the example of FIGS. 3 and 3A, the insulation forming the insulated portions may be any material that can prevent or minimize the conduction of electricity. The insulation of the proximal and/or distal ends of the tips may minimize or prevent short-circuiting in the event the helix 68 and the pin 66 come in contact with one another. Further, in accordance with the disclosed example, the insulation at the proximal ends of both the linear pin 66 and the helix 68 may minimize or prevent certain problems such as, for example, far field sensing and/or abberant tissue stimulation in the event that the tips 50 and 52 are not fully embedded into the desired area 24 of the myocardium at the AVS during implantation. Further, it will be understood that the tips 50 and 52 (i.e., the linear pin 66 and the helix 68) are both retractable and/or deployable such that during delivery the distal ends 56 and 62 do not protrude from the distal end 38 of the lead body 22. Once the helix 68 is in place, the linear pin 66 may be deployed out of the lead body 22 into the myocardium.

Figure 4:
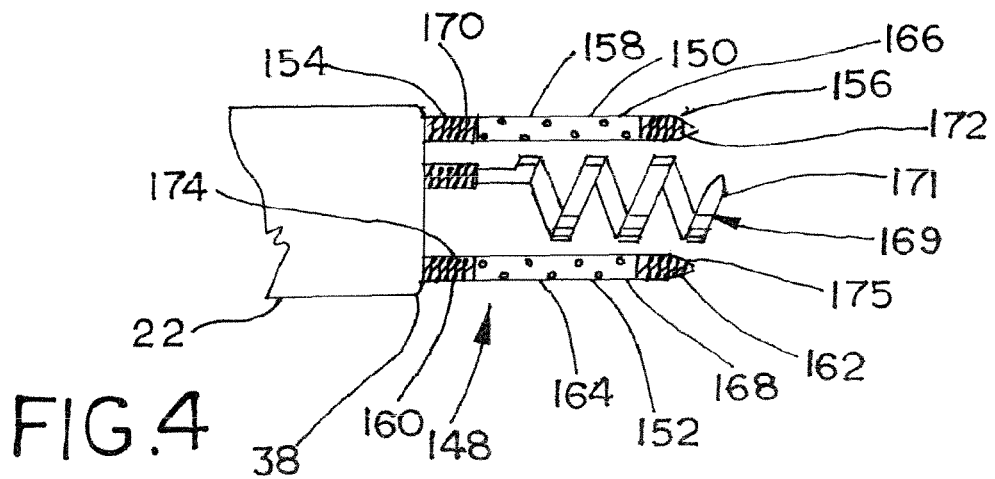
FIG. 4 is an enlarged fragmentary view of the distal end of the lead body and showing a lead tip assembled in accordance with the teachings of a second disclosed example of the present invention.

Referring now to FIG. 4, another embodiment of a tip structure 148 is shown and is assembled in accordance with the teachings of a second disclosed example of the present invention. The tip structure 148 again is attached to the distal end 38 of the lead body 22 with a first tip 150 and a second tip 152 protruding from the distal end 38 of the lead body 22. Once again, the first tip 150 and the second tip 152 are electrically coupled to corresponding electrodes (not shown) in a manner similar to that discussed above with respect to the first disclosed example. The first tip 150 includes a proximal end 154, a distal end 156, and an intermediate portion 158. The second tip 152 also includes a proximal end 160, a distal end 162, and an intermediate portion 164. In the embodiment of FIG. 4, the first tip 150 and the second tip 152 are both in the form of linear pins 166, 168, respectively. In the example shown, the linear pins 166 and 168 have the same length. The tip structure 148 also includes an anchor 169 which, in the example of FIG. 4, is in the form of a helix 171. The tip 150 includes an insulated portion 170 adjacent the proximal end 154, it and an insulated portion 172 adjacent the distal end 156. Similarly, the tip 152 includes an insulated portion 174 adjacent the proximal end 160 and an insulated portion 175 adjacent the distal end 162. In the example of FIG. 4, the insulated portions on each of the tips 150 and 152 has a length measuring the inner range between 5% and 40% of the length of the tips 150 and 152. Preferably, the length of the insulated portions 170, 172, 174 and 175 have a length measuring about 15% of the length of the respective tips, or from about 5% to no more than 15% of the length of the respective tips. Still preferably, the anchor 169 is preferably insulated along its entire length. The intermediate portions 158 and 164 of the tips 150 and 152, respectively, are preferably uninsulated or only partially insulated. In the example of FIG. 4, the pins 166 and 168 may be deployed straight out of the lead body 122 and into the myocardium, preferably at no angle or at only a small angle. The anchor/helix is fully insulated and is not an electrode. Preferably, the lengths of the pins 166 168 can be variable, with the preferred length being about 75% of the effective length of the anchor/helix. Preferably, the effective lengths are measured in the same manner as that discussed above with respect to the first disclosed example.

Figure 5:
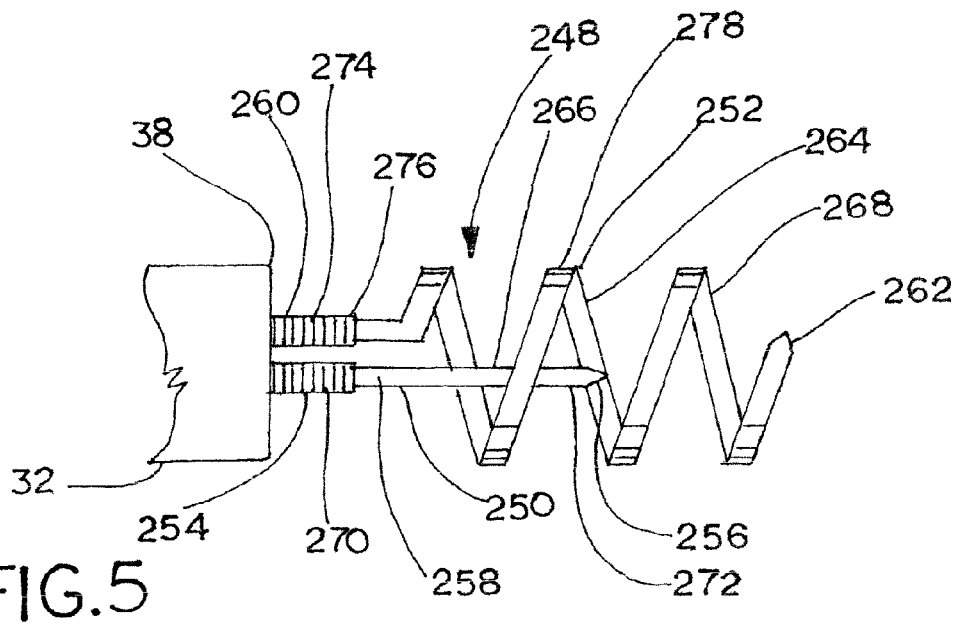
FIG. 5 is an enlarged fragmentary view of the distal end of the lead body and showing a lead tip assembled in accordance with the teachings of a third disclosed example of the present invention.

Referring now to FIG. 5, a tip structure 248 is shown and is assembled in accordance with the teachings of a third disclosed example of the present invention. The tip structure 248 is shown attached to the distal end 38 of the lead body 22, with a first tip 250 and a second tip 252 protruding from the distal end 38 of the lead body 22. The tips 250 and 252 are again electrically coupled to corresponding electrodes (not shown). The first tip 250 includes a proximal end 254, a distal end 256 and an intermediate portion 258. The second tip 252 also includes a proximal end 260, a distal end 262, and an intermediate portion 264. In the embodiment of FIG. 3, the first tip 250 is in the form of a linear pin 266, while the second tip 252 is in the form of a helix 268, with the linear pin 266 having an effective length L1 and with the helix 268 having an effective length L2 (again measured as discussed above). According to the exemplary form of FIG. 4, the effective length L2 is greater than the effective length L1 and, in one preferred form, is approximately 75% of the effective length L2. The tip 250 includes an insulated portion 270 adjacent the proximal end 254 and an insulated portion 272 adjacent the distal end 256. The insulated portions 270 and 272 are fully insulated, and the intermediate portion 258 is uninsulated. Preferably, each of the insulated portions 270 and 272 has a length measuring in a range between 5% and 40% of the effective length L1 of the first tip 250. Still preferably, each of the insulated portions 270 and 272 has a length measuring about 15% of the effective length L1, or alternatively from 5% to no more than 15% of the effective length L1. The helix 268 of the second tip 252 winds around the first tip 250 so as to surround a portion of the first tip 250. The second tip 252 includes an insulated portion 274 adjacent the proximal end 260. The insulated portion 274 is fully insulated, and measures in a range between 5% and 40% of the effective length L2 of the second tip 252. The insulated portion 274 includes an end 276, at which point the insulation transitions to an uninsulated portion 278.

Figure 6:
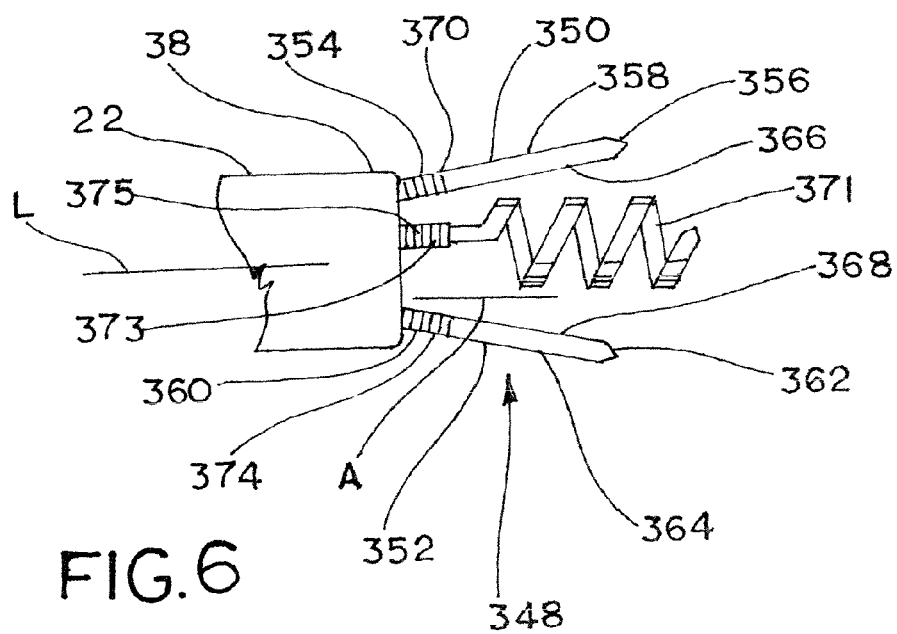
FIG. 6 is an enlarged fragmentary view of the distal end of the lead body and showing a lead tip assembled in accordance with the teachings of a fourth disclosed example of the present invention.

Referring now to FIG. 6, another embodiment of a tip structure 348 is shown and is assembled in accordance with the teachings of a fourth disclosed example of the present invention. The tip structure 348 is similar in some respects to the tip structure 148 discussed above with respect to FIG. 4. In the interest of brevity, only the significant differences between the embodiment of FIG. 6 and the embodiment of FIG. 4 will be discussed in detail, it being understood that all remaining features may be the same or similar with the features discussed above. A first tip 350 and a second tip 352 protrude from the distal end 38 of the lead body 22, with the first tip 350 having a proximal end 354, a distal end 356, and an intermediate portion 358, and with the second tip 352 having a proximal end 360, a distal end 362, and an intermediate portion 364. In the embodiment of FIG. 6, the first tip 350 and the second tip 352 are both in the form of linear pins 366 and 368, respectively. However, in the example shown, the linear pins 366 and 368 are oriented at an angle A relative to the axis L of the lead body 22. Preferably, the angle A measures in the range of five (5) degrees to sixty (60) degrees, with an angle of thirty-five (35) degrees being most preferable. The tip structure 348 also includes an anchor helix 371. The tip 350 includes an insulated portion 370 adjacent the proximal end 354, with the balance of the tip 350 being uninsulated. Similarly, the tip 352 includes an insulated portion 374 adjacent the proximal end 360, with the balance of the tip 352 being uninsulated. The insulated portions on each of the tips 350 and 352 preferably have a length measuring in the range between 5% and 40% of the length of the tips 350 and 352, and more preferably have a length measuring about 15% of the length of the respective tips, or from about 5% to no more than 15% of the length of the respective tips. The anchor helix 371 may have an insulated portion 373 adjacent a proximal end 375 with the balance being either fully insulated, uninsulated, or partially insulated. Preferably, the lengths of the pins 366, 368 can be variable, with the preferred length being about 75% of the effective length of the anchor helix 371.

Referring now to FIG. 7, a tip structure 448 is shown and is assembled in accordance with the teachings of a fifth disclosed example of the present invention. The tip structure 448 again is shown attached to the distal end 38 of the lead body 22 in a manner substantially similar to those embodiments described above. A first tip 450 includes a proximal end 454, a distal end 456, an intermediate portion 458, while the second tip 452 includes a proximal end 460, a distal end 462, and an intermediate portion 464. In the embodiment of FIG. 7, the first tip 450 is in the form of a linear portion 466 from the proximal end of 454 to a boundary or transition 459 adjacent a central part of the intermediate portion 458. After the transition 459, the first tip 450 includes a helical portion 461 extending to the distal end 456. The second tip 452 is in the form of a helix 468. According to the exemplary form of FIG. 7, a combined length L2 of the helical portion 461 and the linear portion 466 is greater than the effective length L2 of the helix 468. Preferably, all of the linear portion 466 of the first tip 450 is insulated, while the helical portion 461 extending from the transition 459 is uninsulated. The second tip 452 preferably includes an insulated portion 472 that measures in a range between 5% and 40% of the effective length L2 of the helix 468. Still preferably, the insulated portion 472 measures about 15% of the effective length L2 of the helix 468.

Referring now to FIG. 8, a tip structure 548 is shown and is assembled in accordance with the teachings of another disclosed example of the present invention. The tip structure 548 is similar in many respects to the embodiment of FIG. 5. Therefore, in the interest of brevity, to the extent practical only the significant differences between the embodiment of FIG. 8 and the embodiment of FIG. 5 will be discussed in detail. A first tip 550 includes a proximal end 554, a distal end 556 and an intermediate portion 558, while a second tip 552 includes a proximal end 560, a distal end 562, and an intermediate portion 564. In the embodiment of FIG. 8, the first tip 550 is in the form of a wire suture 566, while the second tip 552 is in the form of a helix 568. The wire suture 566 preferably is made from a relatively fine gauge wire, and thus may be more flexible relative to the larger gauge, stiffer linear pins employee in other embodiments discussed herein. During deployment, the helix 568 of the second tip 552 is placed into the targeted area 24 of cardiac tissue (preferably AVS or other suitable areas of the myocardium). Then a lumen 569 of a central delivery pin 571 is advanced into the selected area of cardiac tissue, with the delivery pin 571 in turn located within the lumen of the delivery catheter. The delivery pin 571 is then retracted, leaving the wire suture wire suture 566 in place. Preferably, the proximal end 560 of the tip 552 includes an insulate portion 574. Still preferably, the insulated portion 574 measures a range between 5% and 40% of the effective length L1 of the first tip 550, and more preferably about 15% of the effective length L1.

Figure 9:
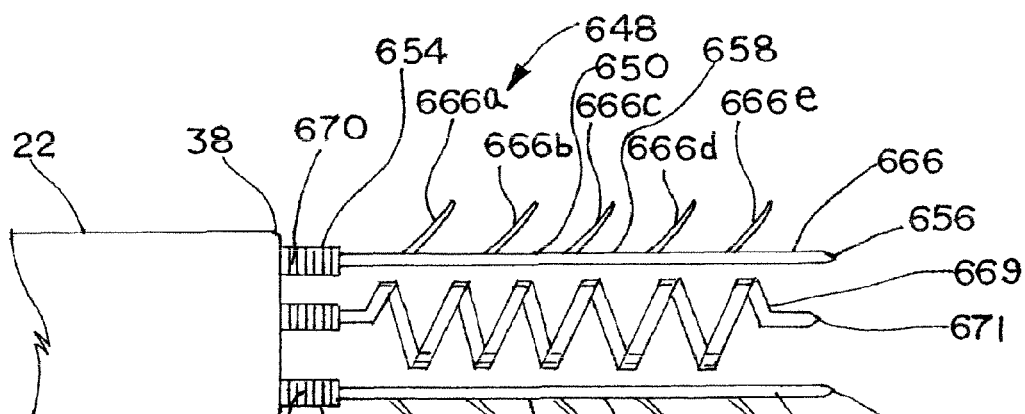
FIG. 9 is an enlarged fragmentary view of the distal end of the lead body and showing a lead tip assembled in accordance with the teachings of a seventh disclosed example of the present invention.

Referring now to FIG. 9, another embodiment of a tip structure 648 is shown and is assembled in accordance with the teachings of a second disclosed example of the present invention. The tip structure 648 again is attached to the distal end 38 of the lead body 22 with a first tip 650 and a second tip 652 protruding from the distal end 38 of the lead body 22. Once again, the first tip 650 and the second tip 652 are electrically coupled to corresponding electrodes (not shown) in a manner similar to that discussed above with respect to the above-described examples. The first tip 650 includes a proximal end 654, a distal end 656, and an intermediate portion 658. The second tip 652 also includes a proximal end 660, a distal end 662, and an intermediate portion 664. In the embodiment of FIG. 9, the first tip 650 and the second tip 652 are both in the form of linear pins 666, 668, respectively. The linear pins 666 and 668 may have the same length and, in the example shown, the linear pins 666 and 668 each include a plurality of laterally extending bristles 666a-e and 668a-e, respectively. The bristles 666a-e and 668a-e preferably are formed of a shape memory material such as nitinol, although other materials may prove suitable. Preferably, the bristles are oriented within the delivery lumen to deploy away from one another. The tip structure 648 also includes an anchor 669 which, in the example of FIG. 9, is in the form of a helix 671. Preferably the bristles 666a-e and 668a-e are arranged to deploy away from the helix 671, although the helix 671 may be insulated. The tip 650 includes an insulated portion 670 adjacent the proximal end 654, while the tip 652 includes an insulated portion 674 adjacent the proximal end 660. The insulated portions on each of the tips 650 and 652 have a length measuring in the range between 5% and 40% of the length of the tips 650 and 652, and preferably measure about 15% of the length of the respective tips, or from about 5% to no more than 15% of the length of the respective tips. Still preferably, the anchor 669 is preferably insulated along its entire length. The intermediate portions 658 and 664 of the tips 650 and 652, respectively, are preferably uninsulated or only partially insulated. In the example of FIG. 9, the pins 666 and 668 may be deployed straight out of the lead body 22 and into the myocardium, preferably at no angle or at only a small angle. Preferably, the length of the pins 666, 668 can be variable, with the preferred length being about 75% of the effective length of the anchor/helix. As an alternative, the separate anchor 669 may be eliminated.

Figure 10:
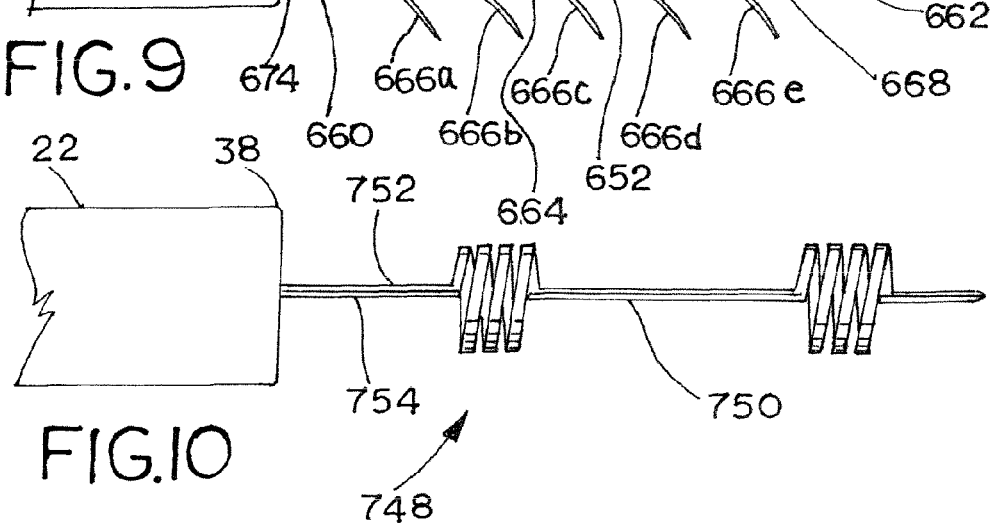
FIG. 10 is an enlarged fragmentary view of the distal end of the lead body and showing a lead tip assembled in accordance with the teachings of a eighth disclosed example of the present invention.

Referring now to FIG. 10, yet a further embodiment of a tip structure 748 is shown and is assembled in accordance with the teachings of the present invention. The tip structure 748 again is attached to the distal end 38 of the lead body 22. A central portion 750 carries a first electrode 752 and a second electrode 754, which are insulated from one another and insulated for the central portion 750. Once again, the electrodes 752 and 754 are electrically coupled to corresponding electrodes (not shown) in a manner similar to that discussed above with respect to the above-described examples. Both of the electrodes 752 and 754 are sized to extend through the lead body 22 so as to extend from the distal end 38.

Figure 11:
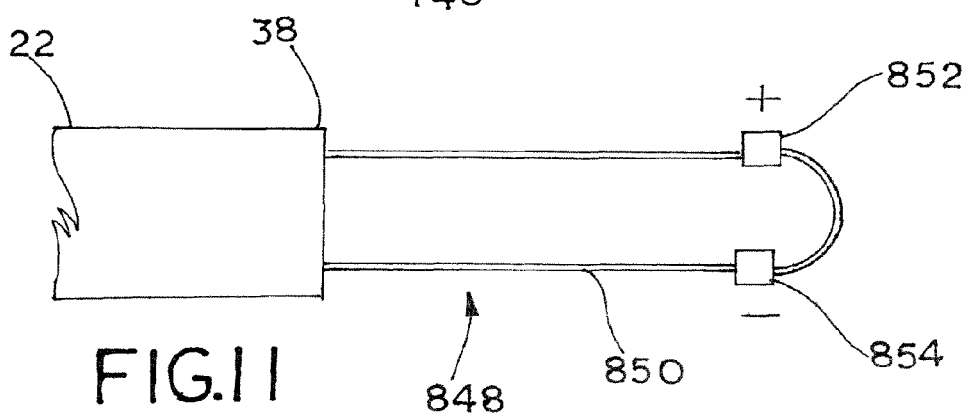
FIG. 11 is an enlarged fragmentary view of the distal end of the lead body and showing a lead tip assembled in accordance with the teachings of a ninth disclosed example of the present invention.

Referring now to FIG. 11, a still further embodiment of a tip structure 848 is shown. The tip structure 848 again is attached to the distal end 38 of the lead body 22. The tip structure 848 includes an insulated wire suture 850, and a first electrode 852 and a second electrode 854 are carried by and spaced along the wire suture 850, which are preferably insulated from one another. Once again, the electrodes 852 and 854 are electrically coupled to corresponding electrodes (not shown) in a manner similar to that discussed above with respect to the above-described examples. The wire suture 850 may be a braided wire formed of multiple insulated wires, which enables the electrodes 852 and 854 to be supported by the wire suture 850 yet remain insulated from one another Preferably, the wire suture is flexible enough to be deployed through a needle into the myocardium or other targeted tissue.

Based on the embodiment disclosed in FIG. 11, the device could be modified to deliver two separate sutures from the same apparatus and may be used for intramyocardial bipolar pacing. By tightening one suture more or less than the other suture, it may be possible to, in effect, have different size electrodes or conduction velocities downstream from one electrode. This arrangement may allow for pacing from more than one location using the same bipolar pair. Further, the wire suture may itself have more than one electrode. The wire suture structure may be used epicardially or endocardially to capture or lasso a piece of myocardium, thus not only working as an intramyocardial electrode, but also as a fixation mechanism.

Figure 12:
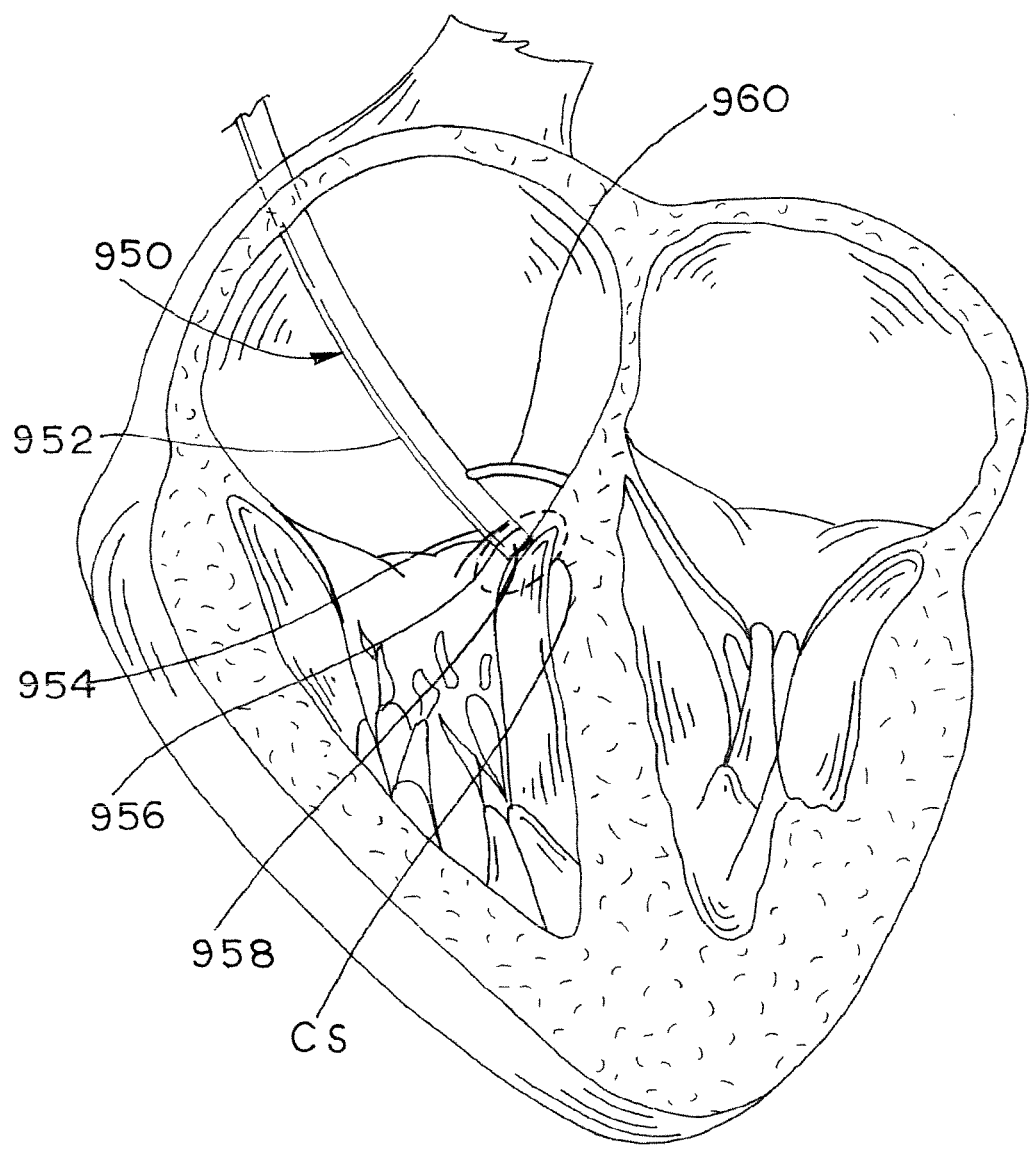
FIG. 12 is a diagrammatic view of a heart illustrating a lead delivery tool assembled in accordance with the teachings of another disclosed example of the present invention and having a branch for registration with an anatomical landmark, such as the coronary sinus, having a known positional relationship relative to the atrioventricular septum to permit placement of a pacing, sensing, or defibrillator lead at the atrioventricular septum.
Figure 13:
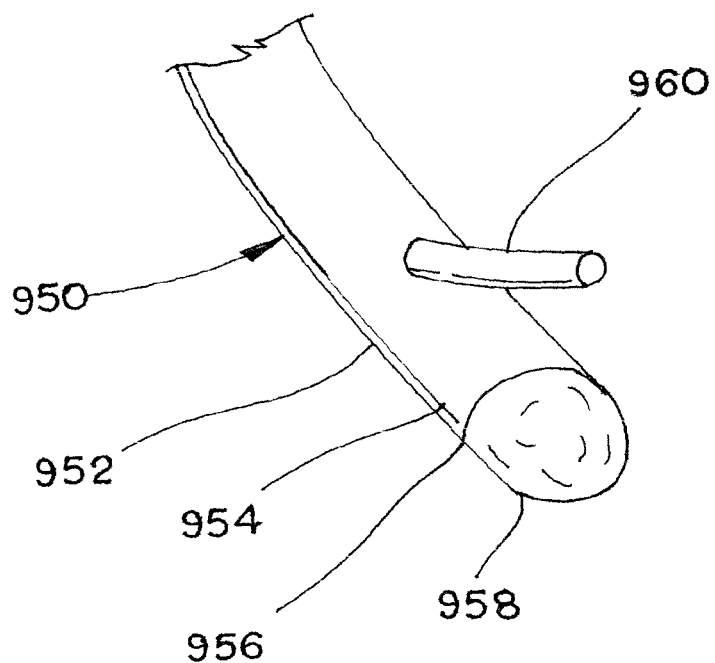
FIG. 13 is an enlarged diagrammatic view of the lead delivery tool illustrated in FIG. 12 and showing a first lumen branch for registration with the anatomical landmark, and a second lumen branch for registration with the atrioventricular septum to permit placement of the electrode lead body at the atrioventricular septum.

Referring now to FIGS. 12 and 13, a lead delivery tool 950 assembled in accordance with the teachings of another disclosed example of the present invention is shown. The lead delivery tool 950 includes a delivery sheath 952 having a curved design that is adapted to cannulate the coronary sinus ostium. Delivery sheaths designed to cannulate the coronary sinus are known and readily available. The lead delivery tool 950 includes a first lumen 954 having a distal end 956 which carries an expandable component 958, which may be a compliant balloon or a nitinol component. The delivery sheath 952 is routed to the opening of the coronary sinus CS, and the expandable component 958 is expanded or inflated to secure the sheath at the coronary sinus. The delivery tool 950 includes a second lumen 960, which branches off the delivery tool 950. The second lumen 960 is sized and located relative to the first lumen 954 such that, when the first lumen 954 is disposed at the coronary sinus, the second lumen 960 will be located adjacent the AVS. Consequently, the second lumen 960 provides a platform to deliver the lead body 22 to the AVS, whereby any one of the above-described examples of the foregoing lead body and tip structures may be routed to the AVS. In further accordance with a preferred form of the invention, the second lumen 960 may include a telescoping pre-formed inner sheath that would accommodate the selected lead body and that would route the lead body closely adjacent the AVS. The first and second lumens 950 and 960 are sized relative to one another on the delivery tool 950 based upon evidence that there is a relatively fixed relationship between the coronary sinus and the AVS. Further, there is evidence that since the coronary sinus and the AVS, at least from the perspective of the right atrial endocardial location, are in relative juxtaposition, they move together during cardiac motion. Accordingly, a sheath stabilized in the coronary sinus ostium may provide a stable platform for deploying an atrioventricular septal lead. The component of the main sheath in the coronary sinus could have a very tiny lumen, simply enough to allow placement of a wire for stability and confirmation of position or injection of contrast to confirm positioned within the coronary sinus. At best, most of the lumen could be made available for the fork or the side hole design for permitting placement of the lead at the AVS. Such a lead may be a "peel away" or "cuttable" lead to allow for lead deployment. Plus, the lead would not have to have a modified proximal end and could use standard IS-1 connectors, which are standard in all current pacemakers and defibrillator pace-sense ports. Finally, the example of FIGS. 12 and 13 may be usable for some patients in whom atrioventricular septal pacing may provide protection against tricuspid regurgitation by not violating the tricuspid valve, but may not effectively resynchronize congestive heart failure. These patients could require an AVS lead at a second lead at the left ventricle (via the coronary sinus). It is conceivable that in a sub-set of patients who may benefit from a lead placed at the AVS, a more traditional left ventricular lead may be placed through the sheath in the coronary sinus into a more traditional left ventricular position. This "forked sheath" would permit placement of both leads using a single sheath and facilitate the implant procedure.

Figure 14:
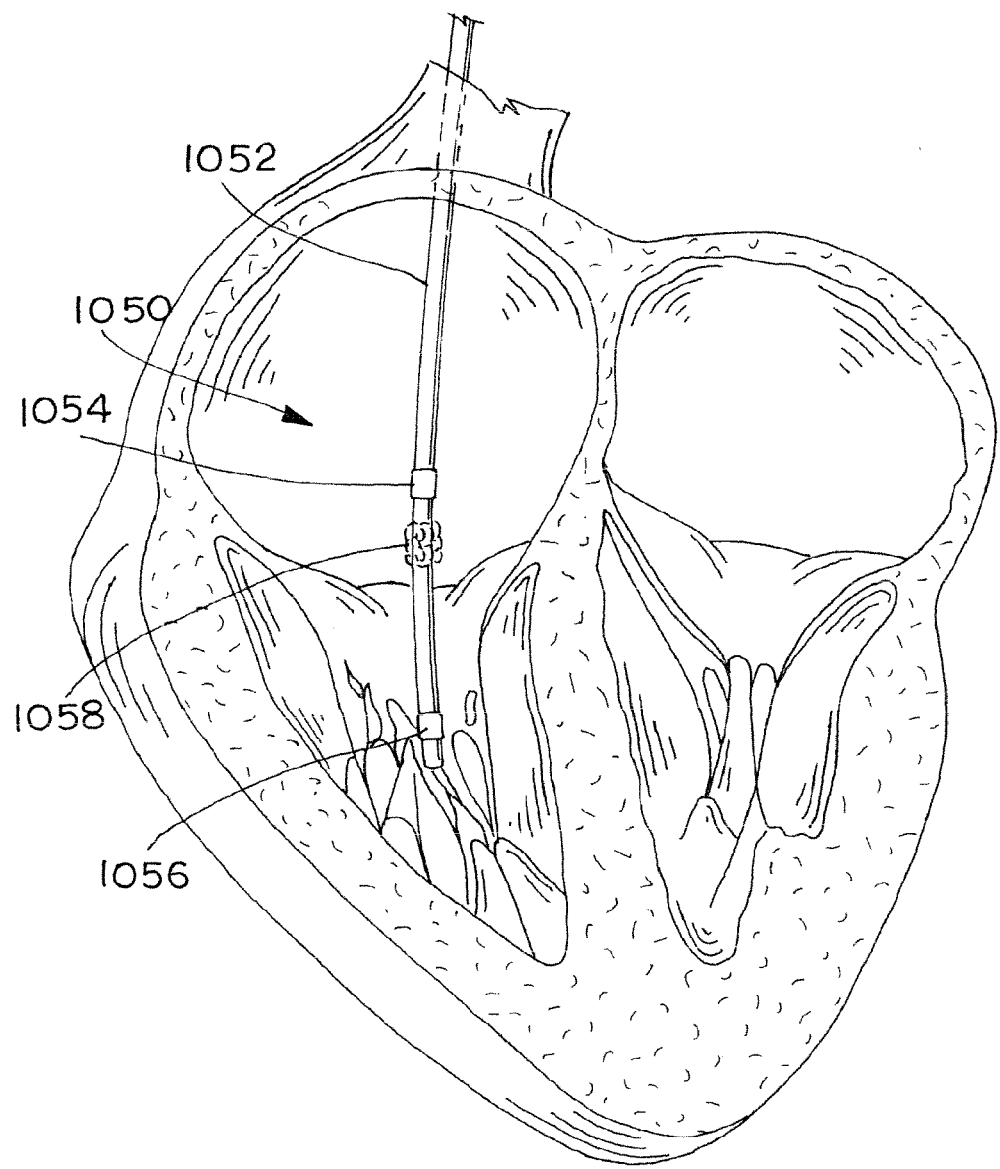
FIG. 14 is a cross-sectional illustration of a heart and illustrating a delivery sheath assembled in accordance with the teachings of a further disclosed example of the present invention and having an undeployed blocking device equipped with a pair of sensors arranged for positioning on opposite sides of the tricuspid valve, wherein the blocking device may assist placement of a separate lead body at the atrioventricular septum.
Figure 15:
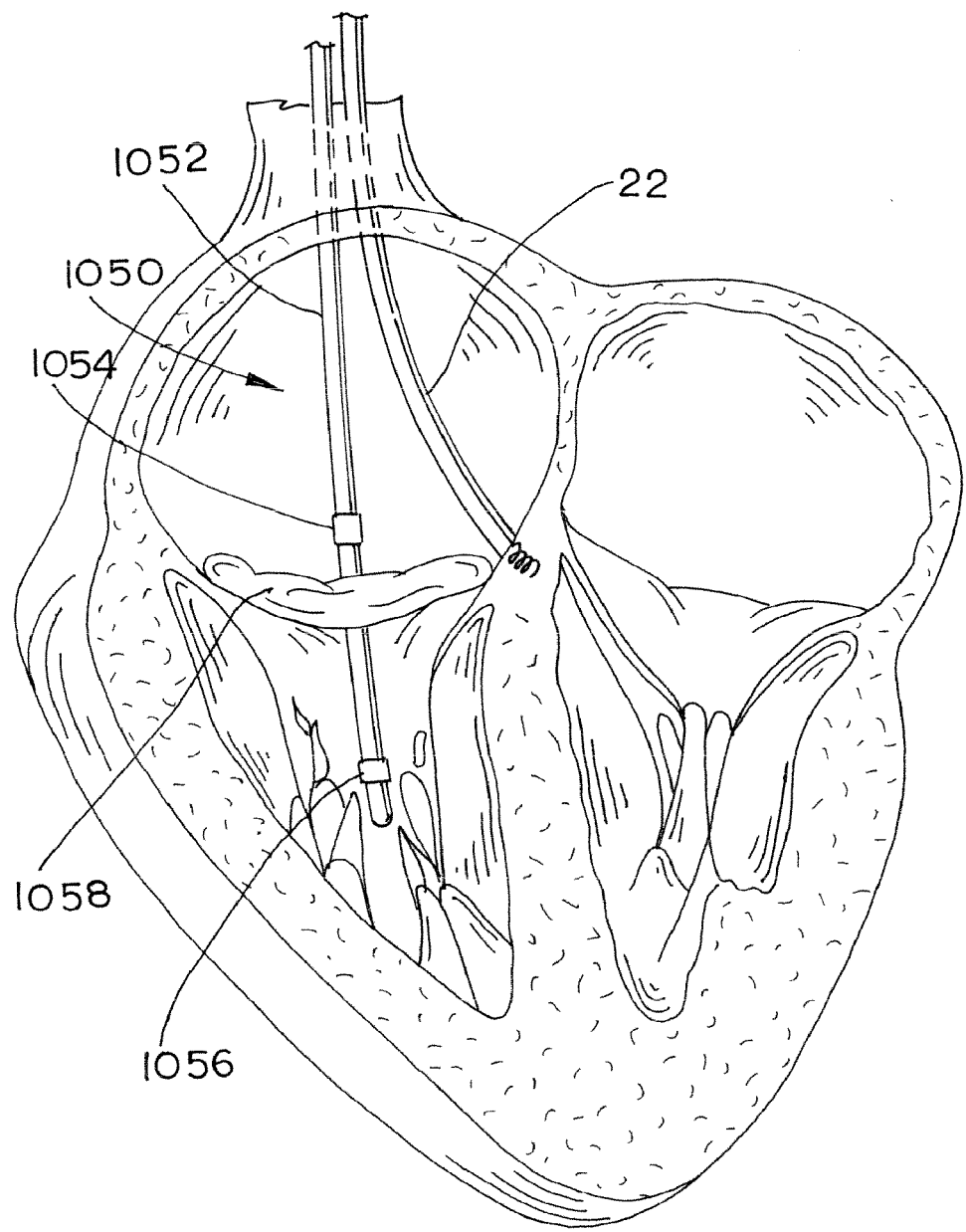
FIG. 15 is a cross-sectional view similar to FIG. 14 and illustrating the blocking device in a deployed state.

Referring now to FIGS. 14 and 15, another delivery tool 1050 is shown. In the example of FIGS. 14 and 15, the delivery tool 1050 includes a delivery sheath 1052 having a proximal sensor 1054, a distal sensor 1056, and an expandable component 1058 located on the delivery sheath 1052 between the proximal sensor 1054 and the distal sensor 1056. The proximal and distal sensors 1054 and 1056 may be, for example, pressure sensors, collectible sensors, or some combination of pressure and electrical sensors. The delivery tool 1050 is positioned such that the proximal sensor 1054 is disposed in the right atrium while the distal sensor is disposed in the right ventricle. Consequently, the proximal sensor reports atrial pressures and electrograms, while the distal sensor reports distal pressures and electograms. Once a physician establishes the correct placement of the delivery tool 1050, with each of the sensors in the appropriate chamber, the expandable component 1058 may be deployed above the tricuspid valve. A lead body, which may be the lead body 22 discussed above with respect to the foregoing examples, can then be deployed out of the delivery sheath 1052 or through a separate delivery sheath (not shown, but which may be the same or similar to any one of the delivery devices discussed herein). The expandable component 1058, which may be an expandable balloon, a memory material, or any other suitable expandable component, keeps the lead body 22 in the right atrium and prevents the physician from accidentally slipping below the tricuspid valve into the right ventricle. In addition to helping to obtain correct placement of the lead body 22 at or adjacent the AVS, this arrangement may minimize or prevent the risk that the lead body 22 slips below the tricuspid valve, thus minimizing or preventing possible damage to the tricuspid valve.

Figure 16:
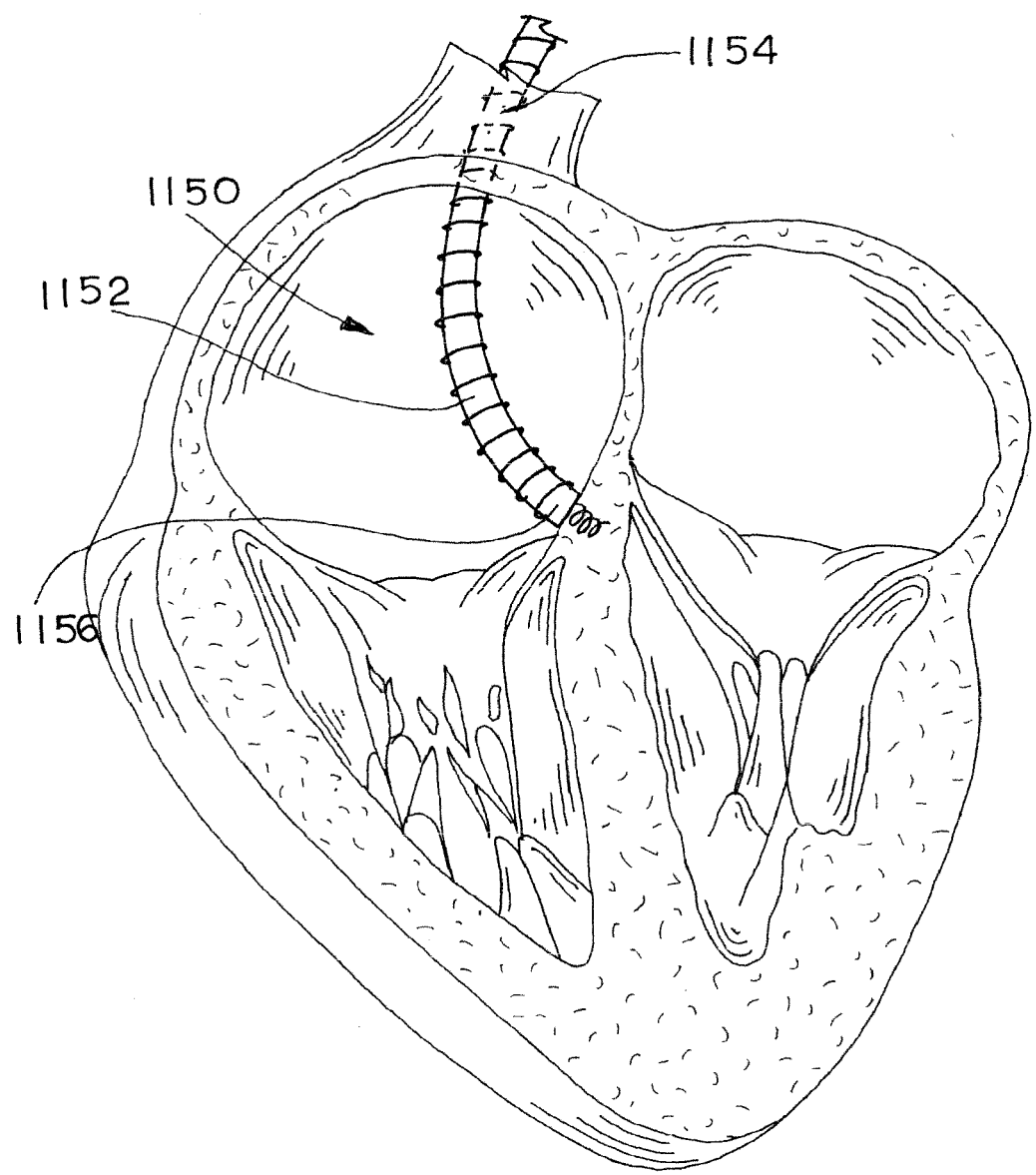
FIG. 16 is another cross-sectional view of a heart and illustrating an implantable cardiac defibrillator (ICD) coil carried on an enlarged delivery sheath which has been routed over a pre-existing lead body for a pacing or sensing device.

Referring now to FIGS. 16-18, another delivery tool 1150 is shown. The delivery tool 1150 assembled in accordance with the teachings of the disclosed example allows for placement of an implantable cardiac defibrillator (ICD) to be deployed over an already placed lead 23 (FIG. 17), which may be a pacing lead, a sensing lead, or any other existing lead. The delivery tool 1150 includes a delivery sheath 1152 having a central lumen 1154 large enough to fit over the lead 23 during deployment, and includes a proximal end (not shown) and a distal end 1156. This "over the lead" (OTL) ICD arrangement is placed over the existing lead 23 and then is secured at the distal end 1156. In the arrangement of FIGS. 16-18, the disclosed design may allow for a CRT-D unit to be created around the AVS pacing lead 23. Thus, the resulting CRT-D does not cross a cardiac valve. In the arrangement of FIGS. 16-18, the coils 1150 may be fixed at the proximal end to the ICD, or may be fixed adjacent the distal end using a deployable anchor 1158 (FIG. 18), which preferably is a helical anchor 1160. Note that in this embodiment the helical anchor can also serve as an intramyocardial ICD coil, to allow for delivery of energy directly into the myocardium. This could allow for better defibrillation thresholds. The ICD coil placed over-the-lead could be placed entirely within the myocardium or with a portion of the coil within the myocardium and a portion outside the myocardium as shown in FIG. 18.

In accordance with another aspect of the disclosed invention, exemplary algorithms may improve ICD performance based on the use of intramyocardial sensing leads. The following examples take advantage of the fact that all pacing and sensing leads may be located completely intramyocardially.

For example, one exemplary algorithm may guide the timing of morphology templates as well as morphology comparison during tachycardia. One of the common modalities of failure of morphology algorithms, which compare the morphology of an electrogram during tachycardia to template morphology recorded during normal rhythm, is the difficulty in aligning the two templates. If there is slight deviation in the peak of the template (which is often used for alignment), or minor change in the onset of the electrogram during tachycardia as compared to baseline (despite being an exact match otherwise), then templates and tachycardia electrograms are said to be different by analysis despite actually being the same. Given the benefit of the intramyocardial fixed reference, alignment errors may be rare or non-existent, as the intramyocardial electrogram would serve as an excellent fiducial point. Thus, the tachycardia intramyocardial electrogram timing point would be used as the reference time and compared to the template intramyocardial electrogram timing point. The far field electrograms would actually then be compared aligned using the intramyocardial electrogram. This approach may minimize or eliminate "phase shift" errors in comparing electrogram morphology.

Next, during tachycardia, it is possible to assess the response of tachycardia during basal/septal VPCs (premature ventricular contractions) placed within the septal myocardium. If placement of such VPCs as either single impulses or burst dissociates the ventricle from the atrium during a 1:1 tachycardia without change in the atrial rate, then an atrial tachycardia is diagnosed. Alternatively, if a burst of pacing from the site results in 1:1 ventriculoatrial conduction, then the pattern of resumption of activity following the pacing could define the arrhythmia mechanism. Thus, if upon discontinuation of pacing there is a VVA (ventricular beat, ventricular beat, atrial beat) pattern, then VT (ventricular tachycardia) is diagnosed and treated. However, if upon termination of pacing there is a VAV (ventricular beat, atrial beat, ventricular beta) or VAAV pattern, then supraventricular tachycardia is diagnosed and no painful/shock therapy is delivered. The fact that there may be available reliable ventricular and atrial sensing permits use of these forms of maneuvers that would be otherwise difficult for the device to interpret. In an alternative approach which could also be complementary, the atrium could be paced. If accelerating the atrium does not accelerate ventricular activation, this indicates VT.

One possible primary differentiation/algorithms for SVT is atrial pacing instead of, or in addition to, ventricular pacing in a pre-programmed zone. For slower arrhythmias, atrial pacing may terminate an atrial flutter or transiently slow sinus tachycardia. In addition, if AV nodal conduction is good, then a VT may be terminated possibly easier than pacing the ventricle itself. If AV nodal conduction is poor, then dissociation or variable AV intervals will result, thus suggesting ventricular tachycardia. Simultaneous atrioventricular pacing could also be considered during charge. Thus, it may be desirable to incorporate such an algorithm into a device. In so doing, the device may be coupled to one or more of the lead structures disclosed herein, and the device could have another electrode, which may be the type found in standard leads that are not intramyocardial, and then use that additional lead to pace the atrium and use the intramyocardial lead to pace the ventricle. If such an arrangement is combined with the ICD, this would be useful as a single lead, not necessarily for atrial pacing, but specifically for this differentiating algorithm. See, for example, FIG. 42, which shows an exemplary pair of electrodes A and B for placement in the myocardium, and the additional ring electrode C which may be a standard ring electrode and which is no placed into the myocardium. Those of skill in the art will understand that the electrodes A and B may be replaced with any of the other lead tip/electrode designs outlined herein.

Figure 42:
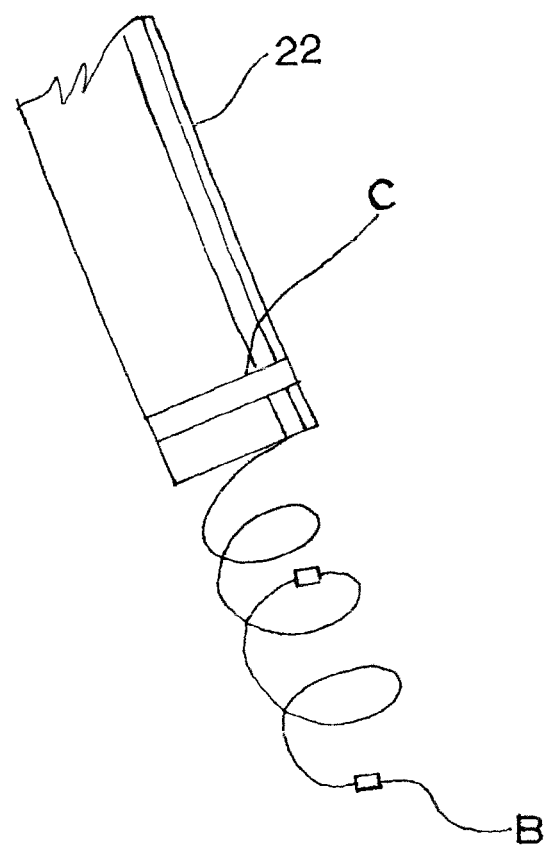
FIG. 42 is an enlarged fragmentary view illustrating an exemplary lead tip having a plurality of intramyocardial electrodes disposed on a helix, and also having an additional ring electrode disposed on the lead body, with the additional ring electrode being non-intramyocardial and suitable for use in pacing, for example, the atrium.

In the approach of FIG. 42, the device may be used to pace the atrium when delivering anti-tachycardia pacing to diagnose the mechanism of the arrhythmia and to treat the arrhythmia. For example, one may employ the following exemplary steps: 1) pace the atrium, via the ring electrode C; 2) if arrhythmia terminates, then do nothing more; 3) if the arrhythmia does not terminate, then compare the atrial rate to the ventricular rate; 4) if the atrial rate is greater than the ventricular rate, then do nothing; and 5) if the ventricular rate is more than the (paced) atrial rate, then shock the heart/ventricle with the ICD. This approach may allow for potentially treating supraventricular arrhythmias and disassociating the atrium from the ventricle so as to allow for a more accurate diagnosis of the tachycardia mechanism.

Next, if there were to be more than two electrodes within the myocardium, we could then make actual vector velocity and directionality determination of wave front propagation within the muscle either across the septum or from apex to base or base to apex depending on how the lead replaced. The positioning of multiple intramyocardial electrodes would allow actual measurement of conduction of velocity and directionality from one electrode to the next. Recording these patterns during a baseline normal rhythm and comparing them during a tachycardia would further permit differentiation of SVT (supraventricular tachycardia) from VT.

Further, the differential response to high and low output pacing from the intraventricular septum tachycardia and normal rhythm may also permit differentiation between SVT and VT.

Also, intratmyocardial electrodes could be a way of electrically causing transient AV (atrioventricular) nodal block, if high energy output or very low energy intramyocardial shock can reliably introduce block. Shock delivered in a right ventricular coil results in frequent right bundle branch block that may last a short period of time, for example a minute or two. If a reliable AV node block that is short lived can be developed, then this would be of beneficial in determining the mechanism of arrhythmia and could prove to terminate many supraventricular arrhythmias. Thus, this could be uniquely therapeutic and diagnostic.

Finally, if an atrial electrogram recorded by an intramyocardial atrial lead is used, then it is possible to know reliably when p wave activity is occurring. Thus, it is possible to exclude the p wave by digitally subtracting it from far field electrograms to reliably analyze the electrograms for morphology (if there is 1:1 VA conduction during a tachycardia).

In accordance with one or more of the above-described exemplary forms of the invention, better sensing of cardiac activity may be possible. In one or more exemplary forms, better sensing allows better performance of ICD's, and places less of a burden on adjusting control algorithms which, in prior systems, typically had to be adjusted to account for poor signal quality. Further, in accordance with one or more exemplary forms discussed above, the present invention may provide better sensing and better pacing of ICD's or other devices by placing both the pacing lead and the sensing lead into the myocardium.

It has been discovered that, in some circumstances, it may be advantageous to restrict, limit, or otherwise contain the delivery of the IM electrodes to the myocardium within to a single moving delivery element. To facilitate the delivery of both electrode poles into the myocardium within a single moving platform or element, several exemplary additional embodiments have been developed for the lead tip assembly.

Figure 21:
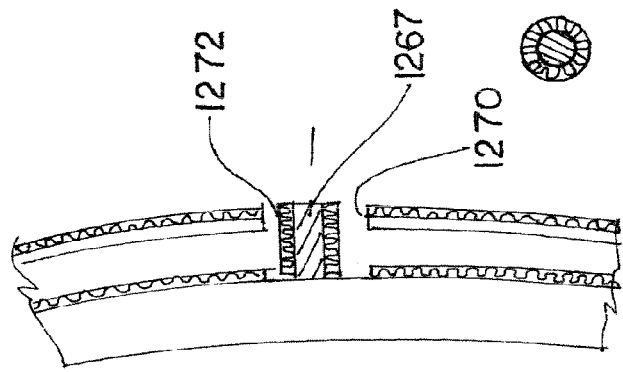
FIG. 21 is an enlarged fragmentary view, partly in section, of another aspect of a double helix lead tip in which an insulated connector plug extends from the inner helix through an aperture in the insulated outer helix.
Figure 20:
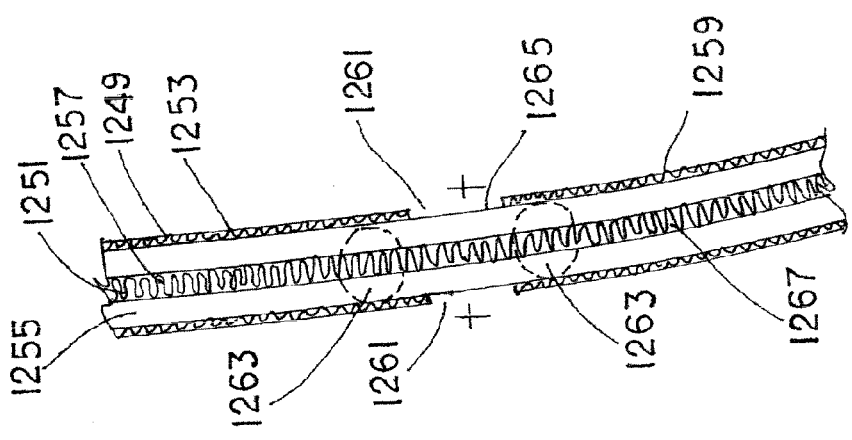
FIG. 20 is an enlarged fragmentary view, partly in section, of the double helix construction of FIG. 19 and illustrating a first set of holes or apertures in the insulation surrounding the outer helix, as well as a second set of holes or apertures through the outer helix and extending through the insulation and all the way to the inner helix.
Figure 19:
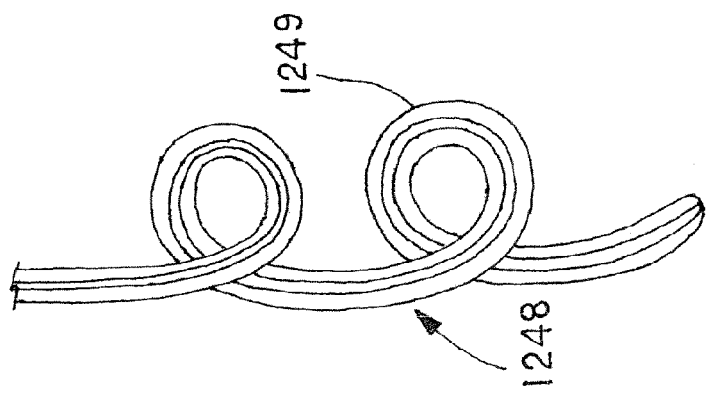
FIG. 19 is a schematic view of a lead tip assembled in accordance with the teachings of a still further disclosed example of the present invention and comprising an insulated inner helix surrounded by an insulated outer helix.

Referring now to FIGS. 19-21, another exemplary lead tip structure 1248 is shown. The lead tip structure 1248 takes the form of a "helix-within-a-helix." The lead tip structure 1248 may be used in place of one or more of the lead tip structures discussed above. The tip structure 1248 is in the form of a helix 1249. As best as shown in FIG. 20, the helix 1249 includes an inner helix 1251 and an outer helix 1253. The inner helix 1249 extends through a passage 1255 formed by the hollow outer helix 1253. The inner helix 1251 includes insulation 1257, while the outer helix 1253 includes insulation 1259. It will be appreciated that the inner helix 1251 is conductive, as is the outer helix 1253. The insulation applied about the inner helix 1251 prevents electrically conductive contact between the inner helix 1251 and the outer helix 1253. In the example shown, the outer helix 1253 is designated as a positive electrode while the inner helix 1251 is designated as the negative electrode. The polarity may be switched if desired. A gap or hole 1261 is formed through the insulation 1259 on the outer helix 1253 to expose a portion of the conductive outer helix 1253, thus forming an electrode 1265. Alternatively, there may be a series or plurality of gaps or holes through the insulation 1259 on the outer helix 1253 in order to expose additional portions of the conductive outer helix 1253 to form additional electrodes 1265. Another gap or hole 1263 is formed through the outer helix 1253 (through the insulation 1259 and through the exterior or the wall of the outer helix 1253). The gap or hole 1263 extends through the insulation 1257 on the inner helix 1251 in order to expose a conductive portion of the inner helix 1251, and consequently forms an electrode 1267. Again, there may be a series or plurality of gaps or holes extending to the inner helix 1251 to form additional electrodes 1267.

Preferably, both the inner helix 1251 and the outer helix 1253 are fully insulated to prevent contact between the two helixes which would result in short-circuiting. The insulation 1259 on the outer helix 1253 may be etched away (via chemical, laser, or mechanical etching) at various points to create the electrodes 1265. Separately, holes are created within the outer helix, and the insulation is etched away from the inner helix at the same point to create the opposite pole electrode.

Referring to FIG. 21, the electrode 1267 carried by the inner helix 1251 may take the form of an optional connector plug 1268 that extends from the inner helix 1251 through a suitable aperture or hole through the surface of the outer helix 1253. The connector plug 1268 may include insulation 1272. The connector plug 1268 will be in suitable electrical contact with the conductive inner helix 1251. The insulation on the outside of the connector plug 1268 preferably spans the hole 1270 created in the outer helix and thereby prevents short-circuiting. Still preferably, the connector plug 1268 is shaped to correspond to the shape of the hole 1270 in the outer helix 1253. The connector plug 1268 could be fixed in place by a variety of methods (adhesive, welding, physical force, etc.).

Figures 22, 23:
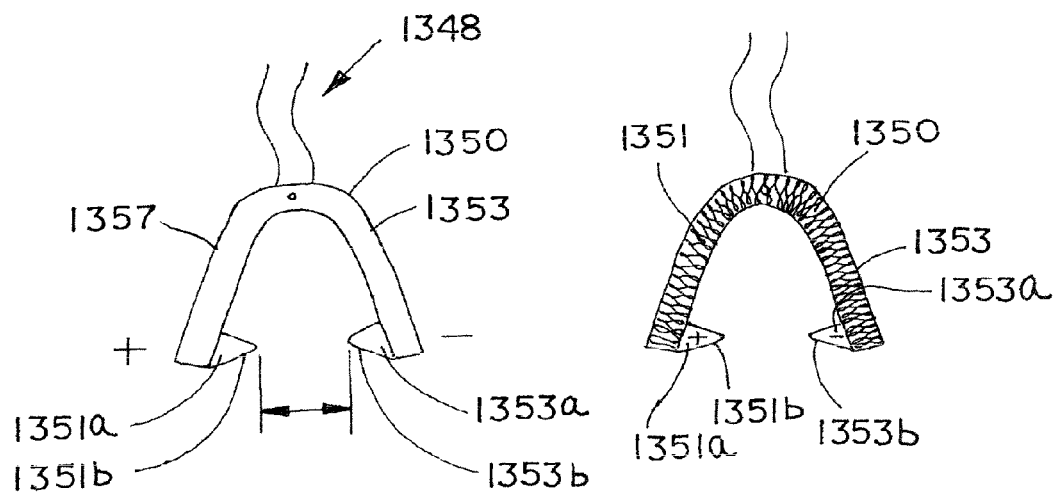
FIGS. 22 and 23 are enlarged views of a lead tip assembled in accordance with the teachings of yet another disclosed example of the present invention and comprising a jaw having a pair of opposed barbed prongs that are insulated from one another and that may be crimped inwardly toward one another to secure the barbed prongs to cardiac tissue.

Referring now to FIGS. 22 and 23, another exemplary lead tip structure 1348 is shown. The lead tip structure 1348 takes the form of a jaw 1350, such as an inwardly crimpable jaw having a first arm 1351 and a second arm 1353. The lead tip structure 1348 may be used in place of one or more of the lead tip structures discussed above. Each arm 1351, 1353 of the lead tip structure 1348 contains or otherwise forms an electrode 1351*a* and 1353*a*, respectively. As shown, each of the electrodes 1351*a* and 1353*a* includes a barb 1351*b* and 1353*b*, respectively. The jaw 1350 would be delivered to the tissue of interest, either in an open state or in a closed state. Preferably, the jaw 1350 then would be used to grasp the tissue to be stimulated and, in the process, drive the electrodes 1351*a* and 1353*a* into the tissue of interest, such as, for example, the myocardium. In one embodiment the arms 1351 and 1353 of the system could be insulated with only the barbed/sharpened tips left conductive. The barbs/tips would embed into the myocardium upon closure of the arms 1351 and 1353 of the jaw 1350. This embodiment may be particularly useful for moderator band pacing. The moderator band is a prominent muscle bundle which crosses from the septomarginal trabeculation to the anterior papillary muscle and then to the parietal wall of the right ventricle.

Figures 24, 25:
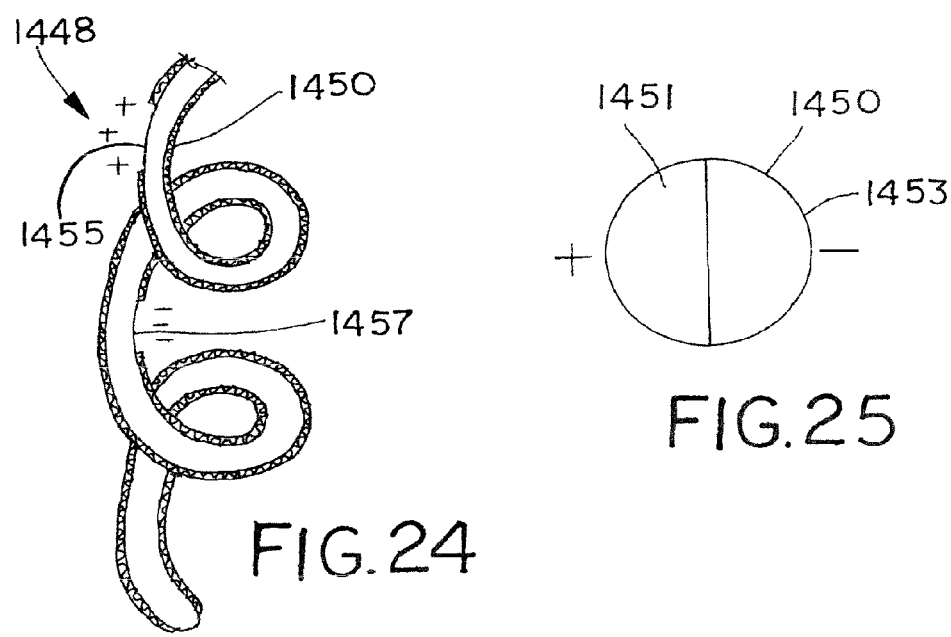
FIG. 24 is a fragmentary elevational view of a lead tip assembled in accordance with the teachings of a still further disclosed example of the present invention and comprising a spliced helix.
FIG. 25 is an enlarged cross-sectional view of the spliced helix of FIG. 24.

Referring now to FIGS. 24 and 25, another exemplary lead tip structure 1448 is shown. The lead tip structure 1448 takes the form of a spliced helix 1450 in which two separate wire halves 1451 and 1453 are bonded together to form the resulting helix 1450. Each half is in electrical communication with a corresponding electrode. Both halves preferably are fully insulated, including along an insulated interface 1454. Portions of the insulation are removed from each of the halves 1451 and 1453 to form the electrodes 1455 and 1457.

Referring now to FIGS. 26 and 27, another exemplary lead tip structure 1548 is shown, and which forms a "braided helix" embodiment. This approach consists of two conducting wires 1551 and 1553 which are first braided together and then formed into a helix 1550. The distal tips 1551*a* and 1553*a* of the two wires can be embedded into a plastic tip 1555 to prevent short-circuiting and to prevent unwinding of the wires. The two wires can be fully insulated, with insulation etched away at conduction sites to form the relevant electrodes 1557 and 1559.

FIG. 28 illustrates an exemplary "hook-wire" anchor or tip structure 1648. This approach again includes of two independent wires 1651 and 1653, each terminating in a distal electrode 1651*a* and 1653*a*. The electrodes 1651*a* and 1653*a* include an anchor element 1655*a* and 1655*b*, respectively, on the distal tip. The anchor element can be any type (a hook, a barb, etc) which preferably functions to secure the wire/electrode structure into the myocardium. A directional guide or ramp 1657 can be used at the distal end of the lead body to direct each wire 1651 and 1653 away from one another during insertion.

FIGS. 29-34 illustrate a lead structure 1748 assembled in accordance with the teachings of still further examples of the present invention. The lead structure 1748 includes a nonconductive helix 1750 having a first externally mounted electrode 1752 and a second externally mounted electrode 1754 spaced apart along the helix 1750. As shown in FIG. 30, the externally mounted electrodes may take the form of a conductive cuff 1755 and 1757. The conductive cuff may be a collar, sleeve, a cylinder, a ring, or any other suitable structure that generally surrounds an adjacent portion of the helix 1750. The cuff 1755 is electrically connected to a first conductive wire 1759 while the second cuff 1757 is electrically connected to a second conductive wire 1761. Alternatively, as shown in FIG. 31, the externally mounted electrodes 1752 and 1754 may take the form of an external wire coil 1763 and 1765, again connected to the wires 1759 and 1761, respectively. In either instance, the wires connecting the conductive elements through the lead body and to the control unit (not shown, but which may be any control unit or ICD as discussed above) would run through the center of the helix within a lumen created within the hollow helix. These wires could be fully insulated as they travel through the lumen of the helix and through the lead body. The helix itself could be made of a non-conductive material such as, for example, plastic, ceramic, or other suitable materials, or the helix may be made from a conductive but fully insulated material. Additionally, an extra layer of insulative protection could be used directly under each conductive element. These extra layers could consist of a relatively hard plastic sleeve placed under each conductive element.

Figure 32:
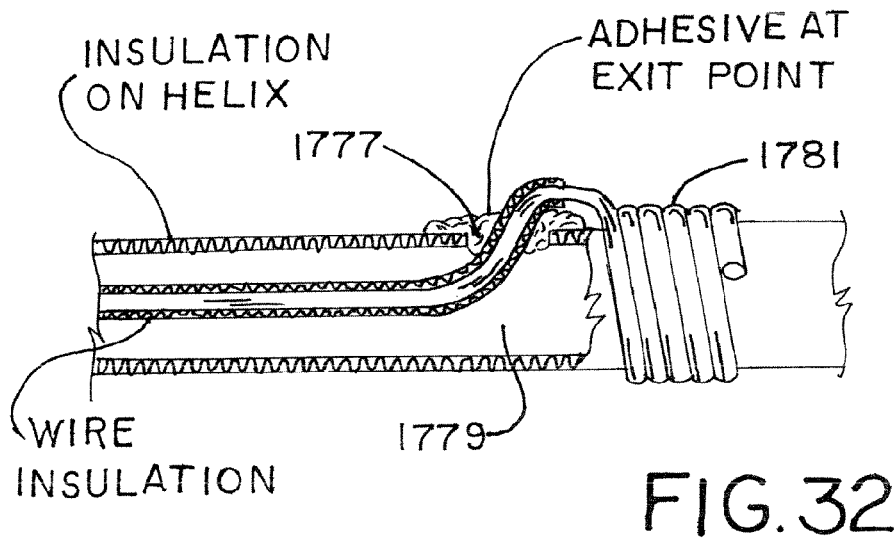
FIG. 32 is an enlarged fragmentary cross sectional view illustrating one exemplary form of routing a wire through the helix of FIG. 29 and routing the wire through the helix such that the wire can be wound around the helix to form an external conductor such as a cuff or coil.
Figure 33:
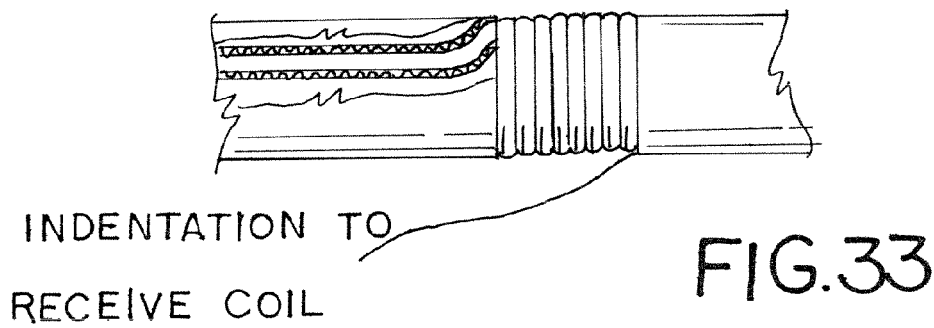
FIG. 33 is an enlarged fragmentary cross-sectional view illustrating another exemplary manner by which a wire may be routed through the helix and wound about the exterior of the helix to form an external cuff or coil in an area of reduced external diameter on the underlying helix.
Figure 34:
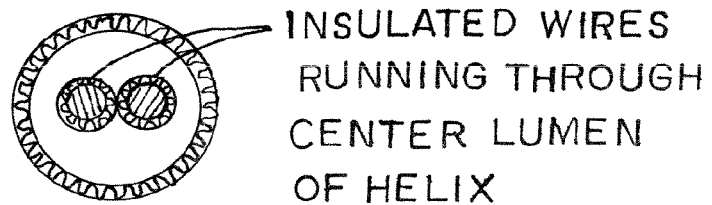
FIG. 34 is an enlarged fragmentary cross-sectional view illustrating a pair of insulated wires running through the center lumen of the helix.

FIG. 32 illustrates one exemplary manner by which any one of the conductive wires 1759 or 1761 may exit the body of the hollow helix 1750. In the example of FIG. 32, the helix 1750 includes a hole 1777 which extends through the exterior of the helix 1750 into a hollow central lumen 1779. As shown, the wire exits the hole 1777, and then begins to wind around an exterior portion of the helix 1750. Alternatively, the wire could exit the central lumen 1779 and be electrically coupled to any one of the aforementioned conductive cuffs. As shown, the wire is fully insulated within the central lumen 1779, and includes an uninsulated portion 1781 which commences after the wire has exited the hole 1777. Preferably, an adhesive or other suitable bonding agent is provided adjacent the hole 1777, which preferably helps to secure the externally mounted conductor to the helix 1750. FIG. 33 is similar to FIG. 32, but illustrates the externally mounted conductor, in this case one of the coils 1763 or 1765, wound about an area 1783 of reduced diameter formed in the helix 1750. Such a construction will preferably help to secure the conduct of element to the helix while allowing the surface of the helix to remain flush or substantially flush. FIG. 34 illustrates the wires 1759, 1761 fully insulated and extending through the central lumen 1779 of the helix 1750.

Figure 35:
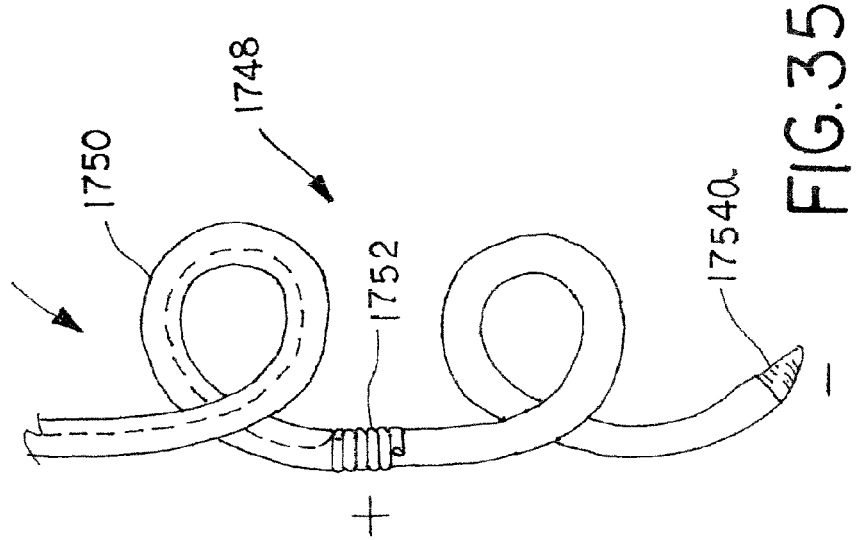
FIG. 35 is an elevational view of a lead tip assembled in accordance with the teachings of a still further disclosed example of the present invention and having an insulated and conductive helix structure carrying an external cuff or coil to form one electrode and having an area of removed insulation, in this case at the distal end of the lead tip, to form another electrode having opposite polarity.

Referring to FIG. 35, another alternative example of the lead tip structure 1748 is shown and again takes the form of the helix 1750. In the example of FIG. 35, the helix 1750 is conductive and fully insulated and includes an externally mounted electrode 1752 similar to either of the cuff or coil arrangements discussed immediately above. However, a second electrode 1754a is formed adjacent a distal tip of the helix 1750 by removing a portion of the insulation adjacent the distal tip.

Figure 36:
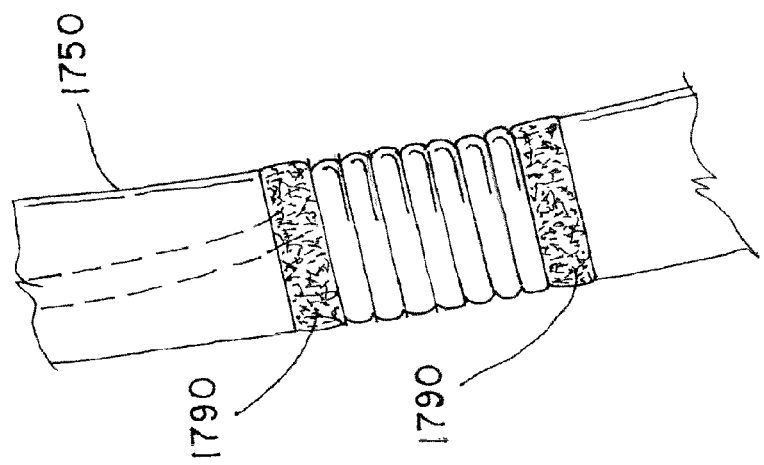
FIG. 36 is an enlarged fragmentary elevational view illustrating the externally formed cuff or coil bounded by a polymer, adhesive, or other bonding agent in order to seal any holes or apertures through the underlying helix and two minimize movement were sliding of the external cuff or coil.

FIG. 36 illustrates any one of the foregoing externally mounted electrodes 1752 or 1754 secured by rings 1790 of a bonding agent, such as a polymer and/or an adhesive. The rings 1790 help to seal the hole 1777 (obscure in FIG. 36 but similar to the hole 1777 discussed above), and further help to prevent the externally mounted electrode from sliding relative to the helix 1750.

Figure 37A:
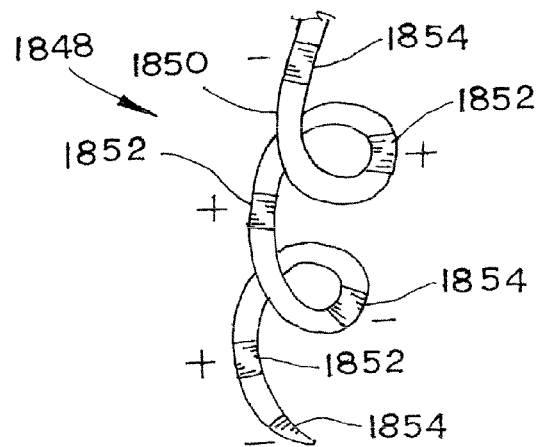
FIGS. 37a, 37b, 37c and 37d are elevational views of further exemplary lead tips, which may be the same or similar to any one of the lead tips shown in FIG. 19, FIG. 24, and/or FIGS. 29-36, with the lead tips provided with multiple electrodes in a symmetrical arrangement as shown in FIG. 37a, an asymmetric arrangement as shown in FIGS. 37b and 37c, or with the electrodes spaced in near-field and far-field pairs as shown in FIG. 37d.
Figure 37B:
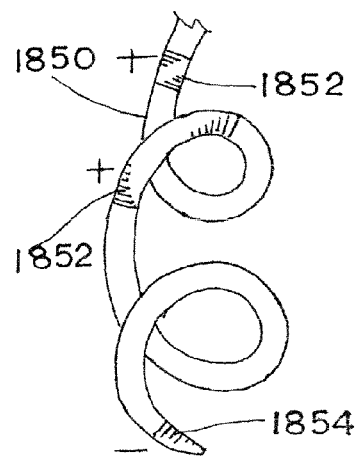

FIGS. 37a through 37d illustrate additional variations on the exemplary lead tip structures discussed herein. The lead tip structures of FIGS. 37a through 37d may be based on any one or more of the foregoing exemplary embodiments. A lead tip structure 1848 as shown in FIG. 37a includes a helix 1850 having multiple positive electrodes 1852 in multiple negative electrodes 1854. In this embodiment, the electrodes are symmetrical, in that there are an equal number of positive and negative electrodes. By comparison, in the example of FIGS. 37b and 37c, again there are multiple electrodes on the underlying helix 1850, but this time there are more positive electrodes 1852 then negative electrodes 1854. Further, in the example of FIG. 37b, not all of the electrodes have the same size. For example, in the example of FIG. 37b, the lower positive electrode is larger than the upper positive electrode, in that the lower positive electrode is longer than the smaller positive electrode.

Multi-electrode designs can be used for a variety of applications. In one instance, they can be used to selectively pace different tissues within the myocardium (see FIGS. 38 and 39 for examples of different tissue areas or tissue planes within the myocardium).

Referring again to FIG. 37b, the negative electrode 1854 is relatively small in disposed at or adjacent a distal tip of the helix 1850. This example has a small distal cathode with two electrodes which serve as the anodes. In this particular embodiment, the cathode is distal and the anodes are proximal. The fundamental concept is that by having electrodes of different sizes, it is possible to preferentially favor capture of the myocardial layer at the level of the smaller electrodes. This results if a similar current passes between a functionally large electrode and a functionally small electrode, the smaller electrode will necessarily have a higher current density. This higher current density increases the likelihood of capture at that particular site. Thus, if an intramyocardial electrode is designed to preferentially pace the deep tissues, mid myocardial layers, or subendocardial layers, the position of the smaller electrodes would be accordingly deployed. This allows a higher level of control of the pacing site and may affect depolarization and repolarization as well as intramyocardial vectors. This embodiment may be particularly useful if deployed from the epicardial surface, since it could cause early endocardial capture, a likely desirable and more normal pattern of activation presently not possible with endocardial electrodes. Preferential pacing of the papillary muscles or other endocavitary structures may also be possible using a variable exposed area/electrode surface area intramyocardial leads.

Figure 37C:
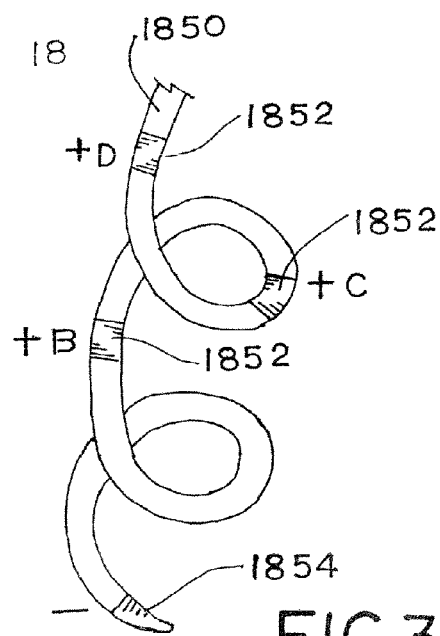
Figure 37D:
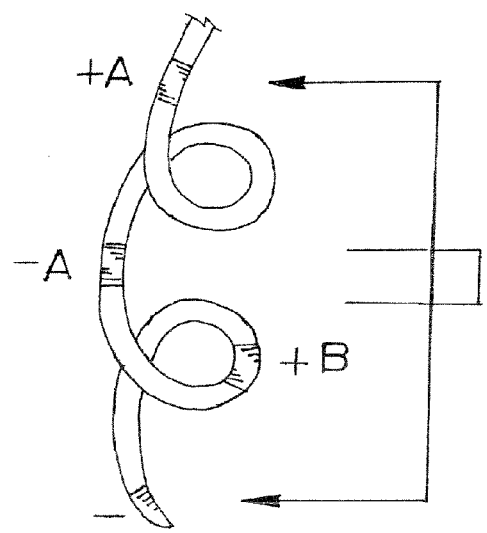

This concept can be further expanded with use of multiple electrodes as shown in FIG. 37c. In this particular drawing, there is a single helix with four different and independently controlled electrodes. As shown, the four electrodes here are of equal size and labeled A (distal most) through D (proximal most). In this arrangement, if the goal was to maximize capture of subendocardial tissues, the electrode D (proximal electrode) would serve as the cathode where as the other three electrodes would be electrically tied together and made the anode. This large anode and small cathode proximally would favor subendocardial capture. Conversely, if the desire were to capture deep tissues, the electrode A would be the cathode with the B, C, and D electrodes joined together to form the anode (this latter option shown in the design of FIG. 37c).

Another application of these multi-electrode designs can be for sensing myocardial electrical activity. Referring to the example of FIG. 37d, this sensing function can be achieved by alternating between a small antennae (near-field myocardial signals) and a larger antennae (far-field myocardial signals). Simultaneous, recordings could be performed between the near-field and between the far-field electrode systems to compare the relative depolarization and repolarization between the deep and more superficial myocardial layers. It is known that there are differences in repolarization between endocardial, mid myocardial, and epicardial tissue layers. Thus, a plurality of electrodes deployed as described would have the capabilities to note differences in repolarizations to each of the myocardial layers. This information may have several potential uses. One could be early detection of ischemia which may differentially affect repolarization of the different tissue layers.

FIGS. 38 and 39 show another sensing benefit of intramyocardial electrodes may be the reduction or elimination of T-wave oversensing. Oversensing of the T wave is a significant clinical problem both with pacemakers but particularly with Implantable Cardiac Defibrillator (ICD) systems. The oversensed T wave can be inappropriately detected as ventricular tachycardia or fibrillation giving rise to increased frequency of inappropriate ICD therapies including shocks. There is no present clear solution to this problem. Various algorithms to vary the sensing parameters and repositioning the lead (a second procedure) are often resorted to but with variable success.

One possible prerequisite to avoiding T wave oversensing may be to have a sufficient margin between the amplitude of the sensed R wave and the sensed T wave (see FIG. 38 for sample ECG tracing). Typically the R wave is significantly larger than the T wave and thus an appropriately set sensing threshold allows detection of ventricular depolarization without detecting the T wave (repolarization). Switching back and forth between different electrode surface sizes or between an intramyocardial bipole, as opposed to a standard bipole, may allow custom fitting the sensed electrogram to most significantly distinguish the R wave from the repolarization wave.

One or more of the exemplary intramyocardial pacing/sensing leads described herein may be used to sense depolarization, as well as repolarization within the myocardium. Suitable positioning of the lead tip, selection of electrode size and, in some iterations (see below), varying the intramyocardial bipoles used for sensing may allow preferential detection at variable depths into the myocardium (subendocardial, variable distance mid myocardial and subepicardial and subendocardial left ventricular). The myocardial cells at each of these layers are different with different durations of the action potential and period of repolarization. Thus, the ratio of the R wave to the T wave will vary at each of these layers and in a given patient a specific layer (say mid myocardial) when sensed will result in a favorable profile of R wave to T wave amplitude minimizing the chance of T wave oversensing. Certain existing leads may not allow for intramyocardial sensing since the anode is not intramyocardial and therefore can not also allow variable sensing based on depth. On the other hand, lead tips assembled in accordance with the teachings of one or more of the examples disclosed herein may allow for the option of picking the intramyocardial depth least likely to result in T wave oversensing (FIGS. 38 and 39).

In some iterations the intramyocardial lead has multiple intramyocardial poles. Preferentially choosing the cathode and anode at a specific depth or separation one from the other, which again in some iterations would be a programmable option enabled by one or more of the specific exemplary leads but programmable through the device interfaced with the lead minimizes the likelihood of T wave oversensing.

FIG. 40 shows a "Helix-Transformer" embodiment. This concept includes the use of coils within the lead body and on the helix to step up or down the voltage delivered from the control unit to the helix. From the basic electronic function of transformers, the voltage of a secondary winding compared to the voltage in a primary winding is equivalent to the ratio of the number of turns on the secondary winding divided by the number of turns on the primary winding (Vs/Vp=Ns/Np). Thus, if we had the secondary winding as the simulating electrode on the helix and having twice the number of turns on this winding as compared to the primary winding in the lead body we could double the voltage at the helix. This could help capture myocardial tissue and possibly save battery life in the control unit. This also may permit capture of local tissue that otherwise would be difficult to capture. The fact that we have a totally intramyocardial electrode may let us have both "terminals" (exposed conductor) on the winding which could be wrapped around the helix.

In FIG. 40, the primary winding is inside the distal end of the lead body. Through the center of the primary winding is the material which will form the helix (i.e. the proximal helix, which within the lead body is straight). Note that the wire consisting of the primary winding is insulated. The helix acts as the transformer core, through which the magnetic flux (but hopefully little electric current) will pass. On the part of the helix which is extended into the myocardium, there is exposed conductor at the proximal end followed by insulated wire wrapped around the helix and then exposed conductor distally. The voltage that is transformed will be developed across the proximal and distal exposed conductor. In the figure shown labeled by the Vs (secondary voltage). The helix would ideally be made of a relatively poor conductor to minimize eddy currents and inefficiency. FIG. 42 shows a lead tip having a plurality of intramyocardial electrodes disposed on a helix, and also having an additional ring electrode disposed on the lead body, with the additional ring electrode being non-intramyocardial and suitable for use in pacing, for example, the atrium.

FIG. 41 depicts a mechanism which may offer enhanced control of distal helix deployment. FIG. 41 shows the use of a stylet 1900 running down the lumen L of the lead so as to engage a drive mechanism 1902 of a helix 1950 to deploy the helix 1950 into the myocardium. The stylet 1900, which is particularly stiff and which has a "squared peg" or other suitable drive shape or drive interface at the distal end fits into the drive mechanism and allows for one to one (1:1) control of the distal helix due to the rotational stiffness of the stylet material. Thus, one turn of the stylet by the operator would result in one turn of the distal helix. Upon completion of lead deployment, the stylet would be removed giving the lead the flexibility necessary for long term survival.

Figure 43:
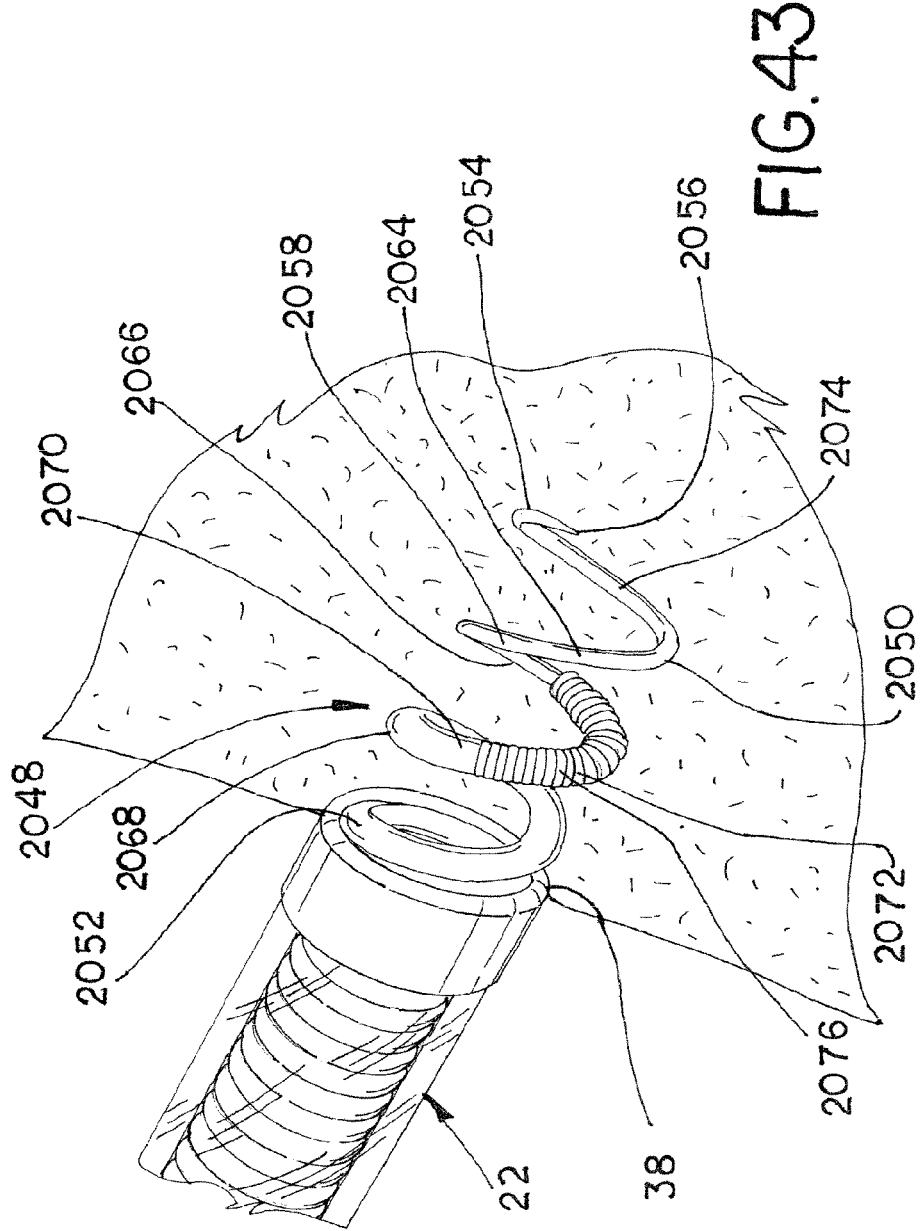
FIG. 43 is an enlarged fragmentary view in perspective of the distal end of the lead body and showing a lead tip assembled in accordance with the teachings of a further disclosed example of the present invention, with the lead tip shown in an anchored state secured to an area of cardiac tissue, such as the AVS.
Figure 44:
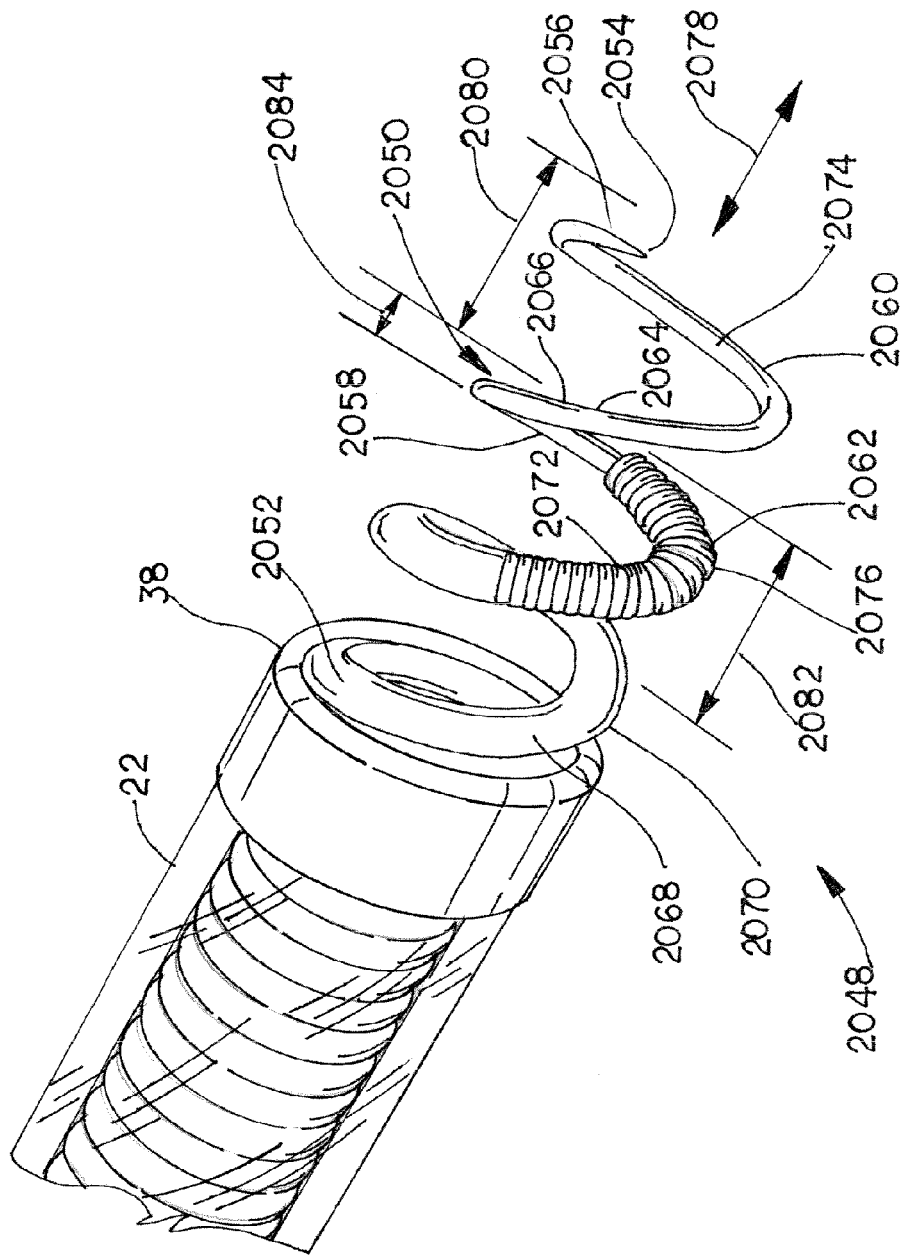
FIG. 44 is a further enlarged fragmentary view in perspective of the lead tip shown in FIG. 43.

Referring now to FIGS. 43 and 44, a preferred embodiment of an electrical lead tip assembly 2048 is shown and is assembled in accordance with the teachings of a still further disclosed example of the present invention. The lead tip assembly 2048 again is attached to the distal end 38 of the lead body 22. In the example shown, the lead tip 2048 includes a helix 2050 protruding from the distal end 38 of the lead body 22. The helix 2050 includes a proximal portion 2052 generally adjacent the distal end 38 of the lead body 22, and distal tip or end 2054. In the example shown, the end 2054 terminates in a sharpened portion 2056, which may aid insertion of the helix 2050 into the desired area of tissue so that the helix 2050 may be suitably embedded into the tissue.

In the example of FIGS. 43 and 44, the helix 2050 includes an insulated portion 2058, which stops short of the end 2054, thus defining a non-insulated section or portion 2060 generally adjacent the end 2054. A coil 2062 covers a portion of the helix 2050. In the example shown, the coil 2062 is applied over the insulated portion 2058 of the helix 2050, but stops short of an end 2064 of the insulated portion 2058, thus forming an exposed section 2066 of the insulated portion 2058. Insulation 2068 covers a proximal portion of the coil 2062, thus defining an insulated portion 2070 of the coil and an exposed or non-insulated portion 2072 of the coil 2062. The helix 2050 and the coil 2062 are both electrically conductive, and both helix 2050 and the coil 2062 are electrically coupled to corresponding conductors or wires that extend through the lead body to the appropriate ICD or other cardiac device (not shown) in a manner similar to that discussed above with respect to the above-described examples. Accordingly, the non-insulated portion 2060 of the helix 2050 forms a first electrode 2074, and the non-insulated portion 2070 of the coil 2062 forms a second electrode 2076. The first electrode 2074 and the second electrode 2076 are spaced apart from one another by the exposed section 2066 of the insulated portion 2058. It will be understood that the helix 2050 and the coil 2062, as well as their respective conductors or wires, are electrically insulated from one another.

As shown in FIG. 44, the non-insulated portion 2060 of the helix 2050 has a length 2080, which may be measured either along the winding of the helix, or which may be measured parallel to a longitudinal axis 2078 of the helix 2050. Similarly, the exposed portion 2072 of the coil 2062 has a length 2082, and the exposed section 2066 has a length 2084, both of which may be measured in the same possible manners.

Figures 45, 46:
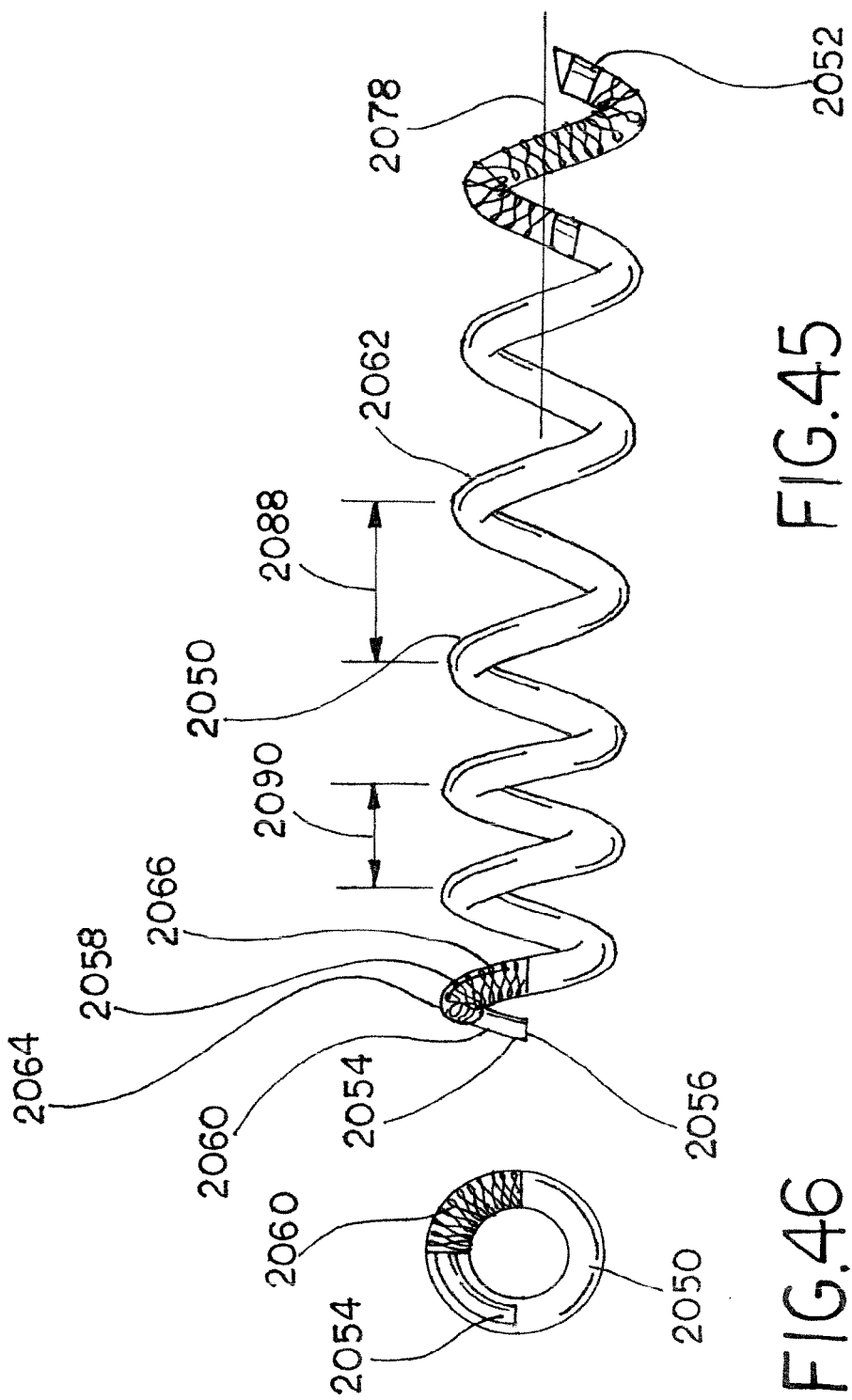
FIG. 45 is an enlarged elevational view of an exemplary helix for use in the lead tip of FIGS. 43 and 44.
FIG. 46 is left side elevational view of the helix of FIG. 45.

Referring now to FIG. 45, the exemplary helix 2050 has a first pitch 2088 in a first section adjacent the end 2054, and a second pitch 2090 adjacent the proximal portion. The end view of FIG. 46 illustrates the manner by which the insulated portion 2058 terminates leaving the exposed non-insulated portion 2060 to form the first electrode 2074. Both figures illustrate how the first and second electrodes 2074 and 2076 are separated from one another by the exposed section 2066.

Referring now to FIGS. 47 and 47A, in the example shown therein the coil 2062 is formed from braided wires 2092, with the braided wires 2092 being wrapped around the insulated portion 2058 of the helix 2050 in a plurality of windings. As shown in FIG. 47A, the braided wires 2090 may be a plurality of individual wires and, in the example shown, there are three individual wires.

Referring now to FIGS. 48 and 48A, in the example shown therein the coil 2062 is formed from a multiple wire assembly 2094, with the multiple wire assembly 2094 being wrapped around the insulated portion 2058 of the helix 2050 to once again form a plurality of windings. As shown in FIG. 47A, the multiple wire assembly 2094 is formed from three individual wires wound around the helix in parallel.

Referring now to FIG. 49, in the example shown therein the coil 2062 is formed from a wire mesh assembly 2096, with the wire mesh assembly 2096 surrounding the relevant insulated portion 2058, much like a sleeve. Preferably, the wire mesh assembly 2096 is formed from a plurality of individual wires.

In the example of FIGS. 43-49, the helix 2050 is formed from a conductive material, which may be platinum/iridium, or any other suitable material. The insulation forming the insulated portion 2058 and the insulated portion 2072 may be formed from polyester, parylene, polyimide, or any other suitable material. The length of the non-insulated portion 2060 may be very to optimize performance of the device by allowing changes in impedance and/or tissue capture, or other variables. When assembled in accordance with the disclosed example, the insulated portion 2070 which covers a portion of the coil 20620 preferably operate to prevent current from leaking into a heart chamber in cases where the lead device is not fully deployed and or not fully embedded into the myocardium or other desired area of cardiac tissue. Once again, the insulation over the coil can be very to optimize performance of the device as mentioned above. In the foregoing cases, both the length of the insulated sections and the thickness of insulation may be varied. The coil 2062 can be secured to the underlying helix 2050 (e.g., to the insulated portion 2058) by bonding, gluing, heating, or by any other suitable mechanism in order to prevent the coil from becoming dislodged or unraveled. Moreover, in the examples of FIGS. 47-49, each of the designs shown therein for the coil 2062 preferably are formed from a plurality of wires rather than a single wire arrangement. Consequently, by employing any one of these exemplary configurations, the coil 2062 may still function in the event of breakage of any one of the individual wires.

The foregoing detailed description describes exemplary forms of the contemplated invention or inventions. The details of the various disclosed examples need not be mutually exclusive. Instead, details from one exemplary embodiment may be applied to another exemplary embodiment. Finally, no unnecessary limitations should be understood from the foregoing description. Instead, the appended claims extend to modifications and deviations from the exemplary forms described herein.

What is claimed is:

1. An electrical lead for a cardiac device, the electrical lead comprising:
 a lead body having a proximal end and a distal end, the lead body sized for insertion through a lumen of a steerable catheter;
 an anchor arranged to secure the distal end of the lead body adjacent an area of cardiac tissue;
 a first electrode and a second electrode extending through the lead body, the first and second electrodes each terminating in a tip having a proximal end, a distal end, and an effective length, the tip of the first and second electrodes arranged to extend from the lead body for insertion into the area of cardiac tissue;
 the tip of each of the first and second electrodes including a fully insulated portion on the proximal end, a fully insulated portion on the distal end, each of the fully insulated portions on both the proximal and distal ends having an insulated length measuring between 5 percent and 40 percent of an effective length of the tip, the tip of each of the first and second electrodes further including an intermediate section between the proximal and distal ends having a continuous uninsulated portion,
 wherein the first electrode and the second electrode are electrically connected to a circuit that delivers opposite polarity to the first and second electrodes.

2. The electrical lead of claim 1, wherein the anchor comprises a helical wire.

3. The electrical lead of claim 1, wherein the anchor is fully insulated.

4. The electrical lead of claim 1, wherein the tip of each of the first and second electrodes is linear.

5. The electrical lead of claim 2, wherein the helical wire is fully insulated and exits the lead body generally along an axis of the lead body, and wherein the tip of each of the first and second electrodes is spaced away from the axis.

6. The electrical lead of claim 5, wherein the tip of each of the first and second electrodes comprises a linear pin extending parallel to the axis.

7. The electrical lead of claim 5, wherein the tip of each of the first and second electrodes is disposed at an angle relative to the axis.

8. The electrical lead of claim 7, wherein the angle measures between 5 degrees and 60 degrees.

9. The electrical lead of claim 8, wherein the angle measures 35 degrees.

10. The electrical lead of claim 1, wherein the anchor is helical, and wherein the effective length of the tip of the first and second electrodes is less than the effective length of the tip of the anchor.

11. The electrical lead of claim 10, wherein the effective length of the tip of the first and second electrodes is about 10% to 90% percent of the effective length of the anchor.

12. The electrical lead of claim 11, wherein the effective length of the tip of the first and second electrodes is about 75 percent of the effective length of the anchor.

13. The electrical lead of claim 1, wherein the insulated length on the proximal and distal ends of each of the tips measures about 15 percent of the effective length of each of the tips.

14. The electrical lead of claim 1, wherein the intermediate section has no insulation.

* * * * *